(12) United States Patent  
Suehara

(10) Patent No.: US 9,345,864 B2
(45) Date of Patent: May 24, 2016

(54) METHODS FOR TREATING SINUS OSTIA USING BALLOON CATHETER DEVICES HAVING A SLIDABLE BALLOON PORTION

(71) Applicant: Terumo Kabushiki Kaisha, Tokyo (JP)

(72) Inventor: Satoru Suehara, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 427 days.

(21) Appl. No.: 13/840,607

(22) Filed: Mar. 15, 2013

(65) Prior Publication Data

US 2014/0277072 A1    Sep. 18, 2014

(51) Int. Cl.
*A61M 19/00* (2006.01)
*A61M 29/02* (2006.01)
*A61B 17/24* (2006.01)
*A61M 25/00* (2006.01)
*A61M 25/01* (2006.01)
*A61B 19/00* (2006.01)

(52) U.S. Cl.
CPC ............... *A61M 29/02* (2013.01); *A61B 17/24* (2013.01); *A61B 19/5212* (2013.01); *A61M 25/0097* (2013.01); *A61M 25/0113* (2013.01)

(58) Field of Classification Search
None
See application file for complete search history.

(56) References Cited

U.S. PATENT DOCUMENTS

| | | | |
|---|---|---|---|
| 4,961,738 A * | 10/1990 | Mackin | 606/15 |
| 5,624,380 A | 4/1997 | Takayama et al. | |
| 2005/0085693 A1 | 4/2005 | Belson et al. | |
| 2005/0240147 A1 | 10/2005 | Makower et al. | |
| 2006/0210605 A1 * | 9/2006 | Chang et al. | 424/434 |
| 2007/0073269 A1 | 3/2007 | Becker | |
| 2008/0097159 A1 | 4/2008 | Ishiguro | |
| 2009/0187098 A1 * | 7/2009 | Makower et al. | 600/424 |
| 2012/0253123 A1 | 10/2012 | Shimizu et al. | |
| 2012/0259217 A1 * | 10/2012 | Gerrans et al. | 600/435 |
| 2013/0030458 A1 * | 1/2013 | Drontle et al. | 606/196 |
| 2013/0066358 A1 | 3/2013 | Nalluri et al. | |

FOREIGN PATENT DOCUMENTS

WO    WO-2006/034008 A2    3/2006

OTHER PUBLICATIONS

US Office Action, U.S. Appl. No. 13/776,057 issued Jul. 14, 2015.

* cited by examiner

*Primary Examiner* — Tuan V Nguyen
(74) *Attorney, Agent, or Firm* — Foley & Lardner LLP

(57) ABSTRACT

A method comprises providing a balloon catheter device; locating a balloon portion within a paranasal sinus ostium while the balloon portion is in the first position such that a distal end of the balloon portion is at a distal end of a paranasal sinus ostium; inflating the balloon portion while the balloon portion is located in the paranasal sinus ostium such that at least a portion of the paranasal sinus ostium is dilated; sliding the balloon portion back to a second position while leaving the distal end of a guide member at the distal end of the paranasal sinus ostium; and viewing an image provided by a camera to determine whether an entirety of the paranasal sinus ostium has been dilated.

16 Claims, 16 Drawing Sheets

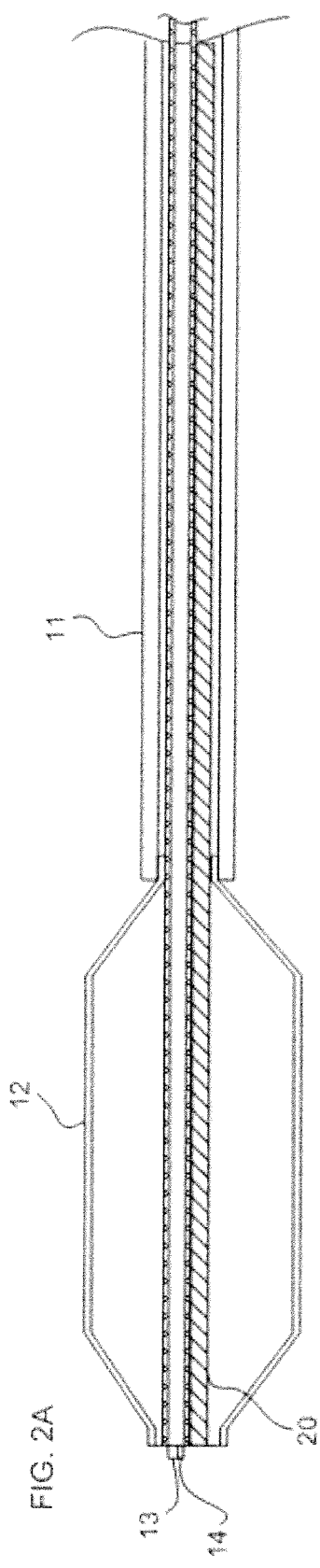
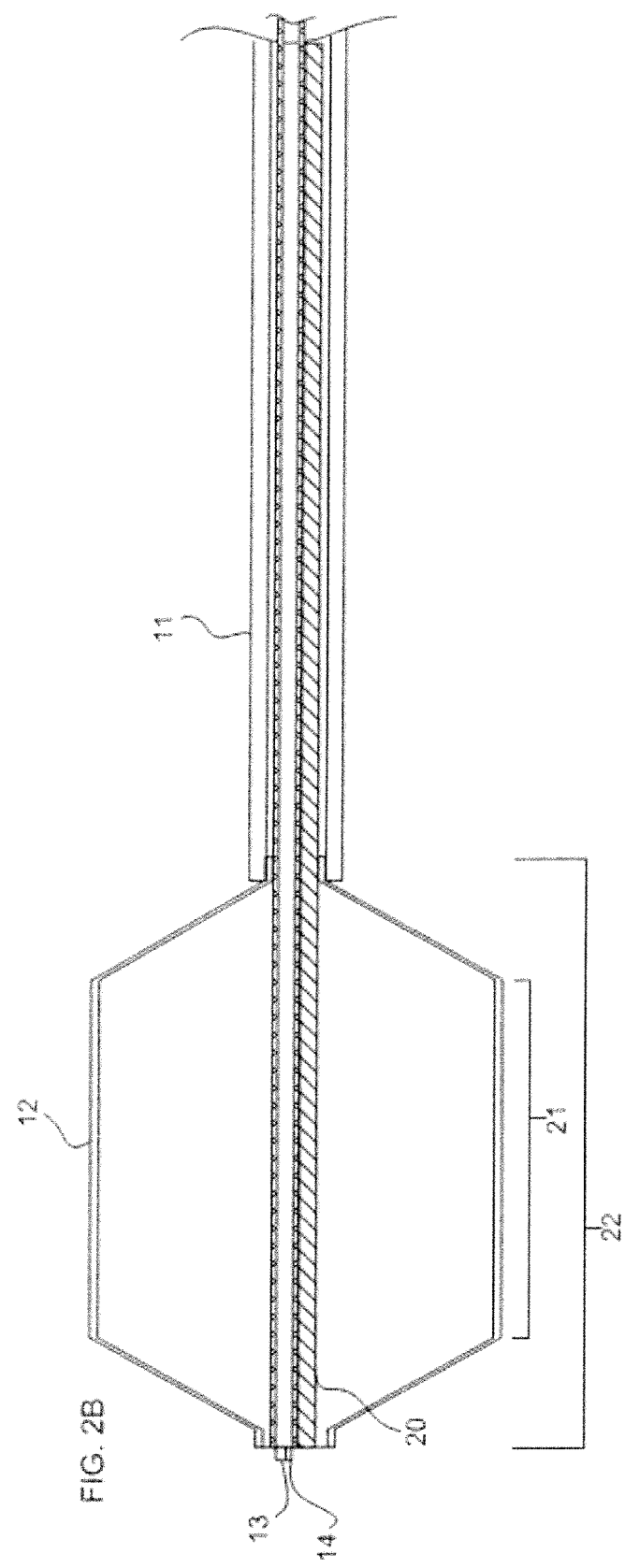

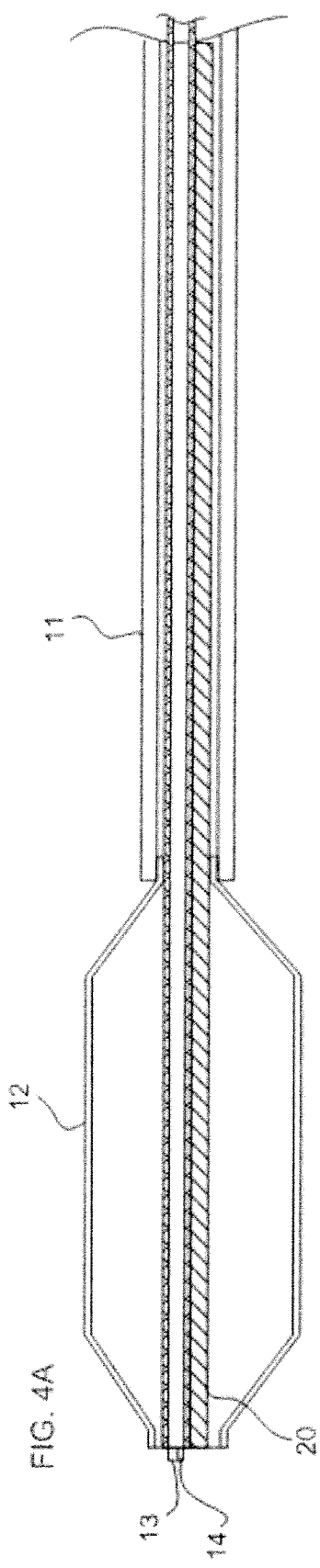
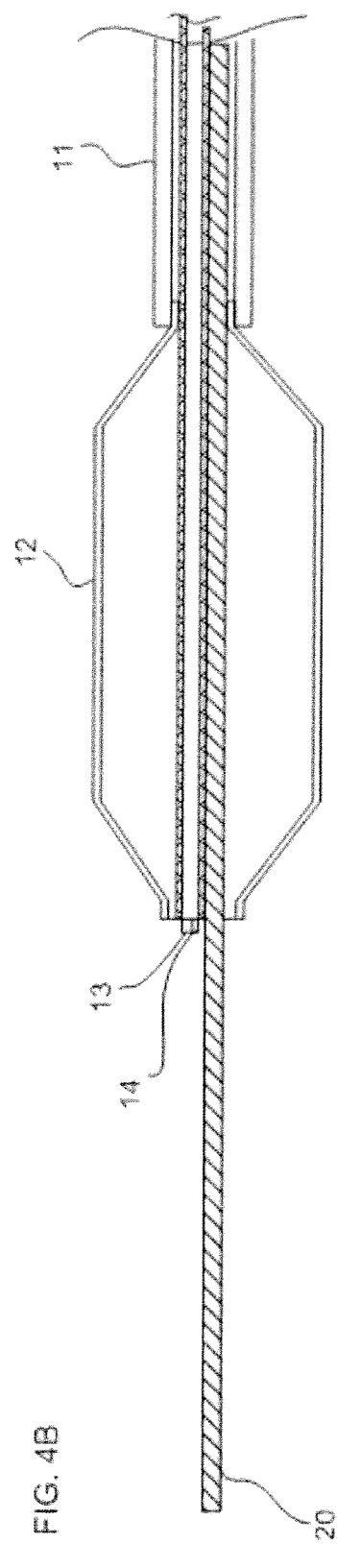
FIG. 4A
FIG. 4B

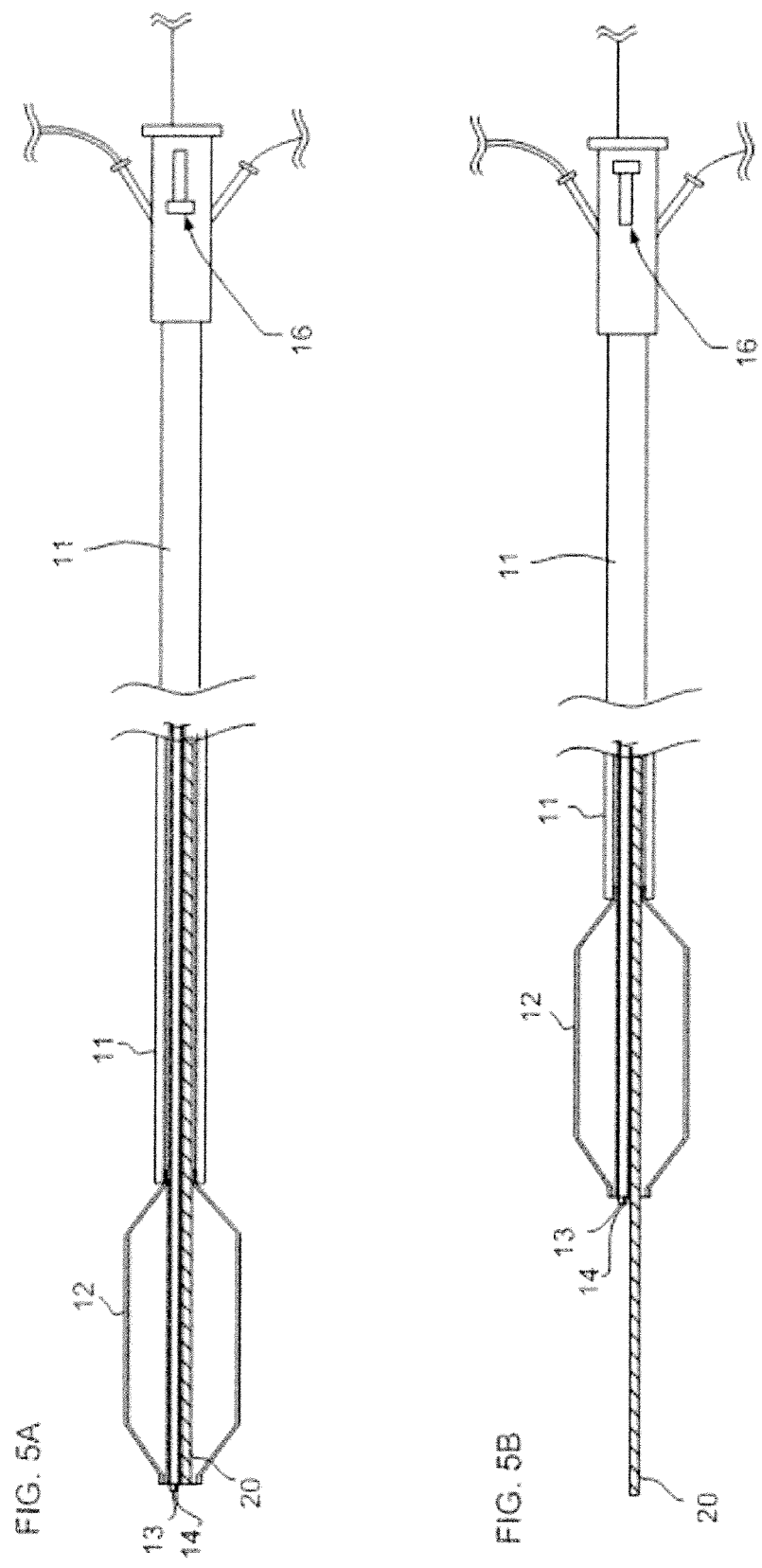

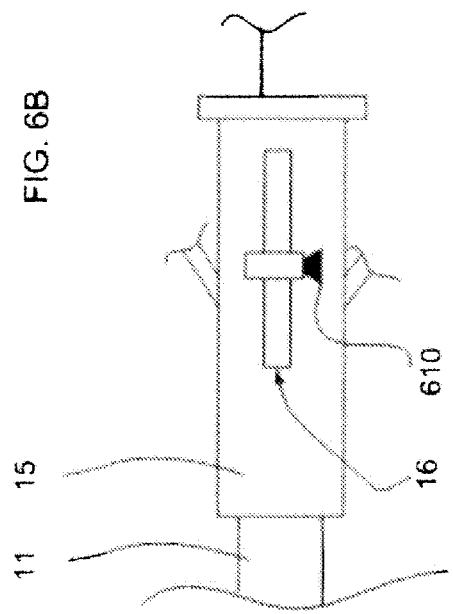
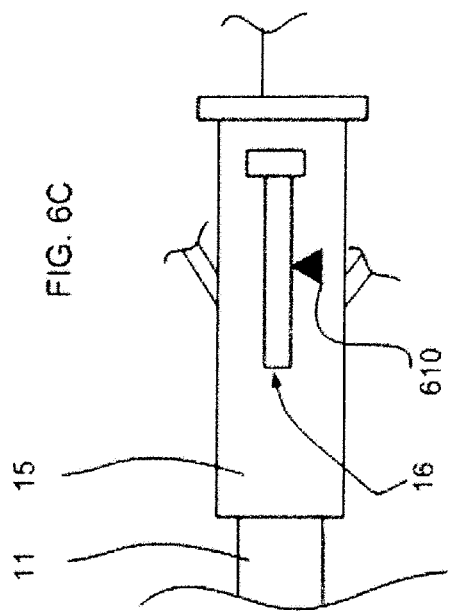
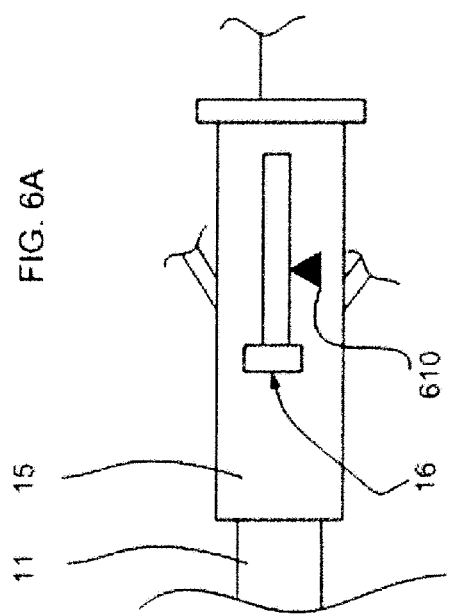

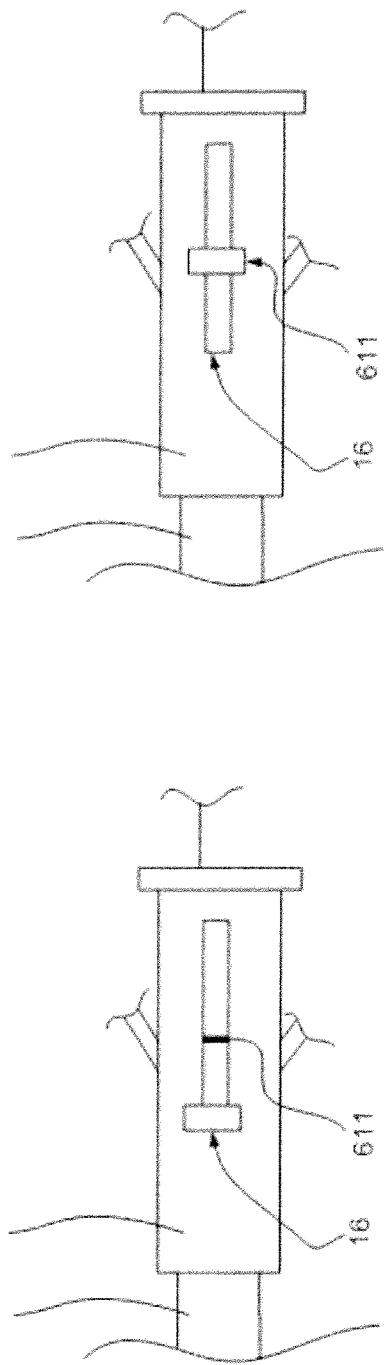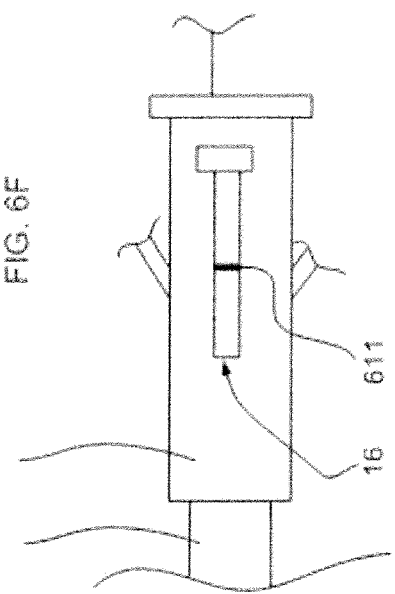

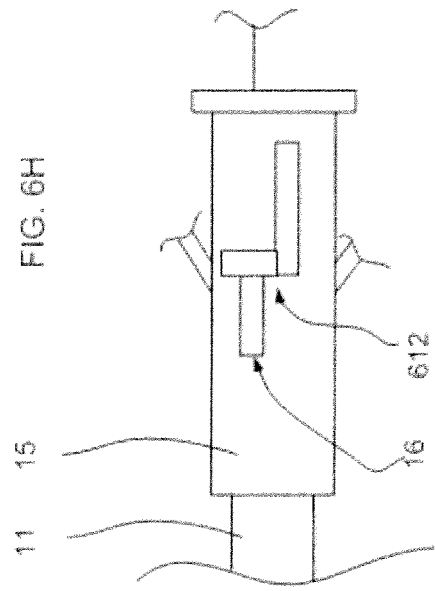
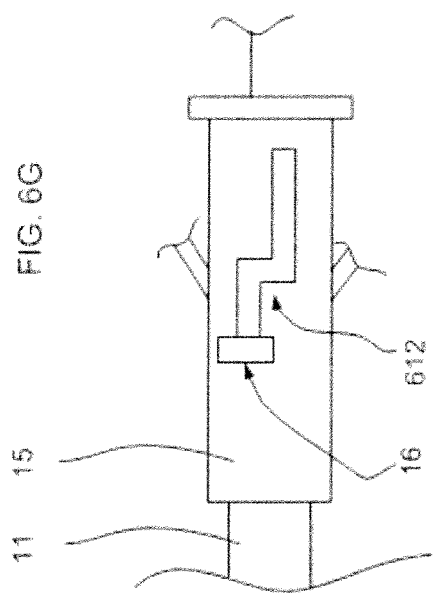
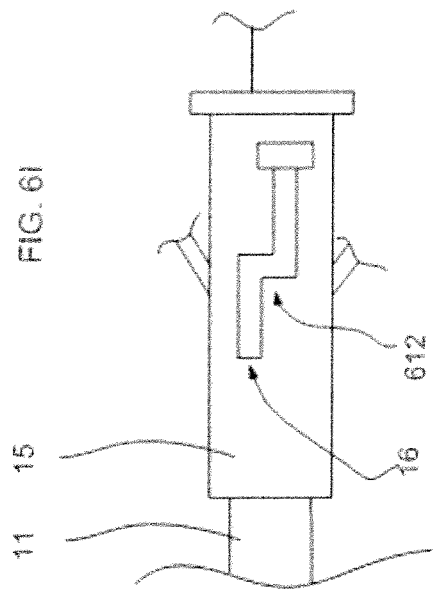

FIG. 8
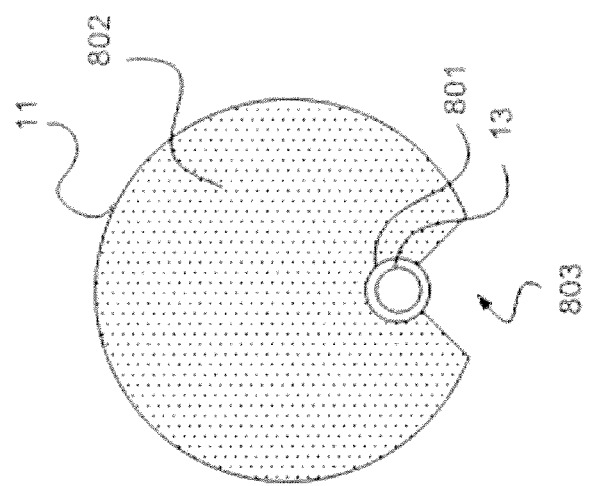
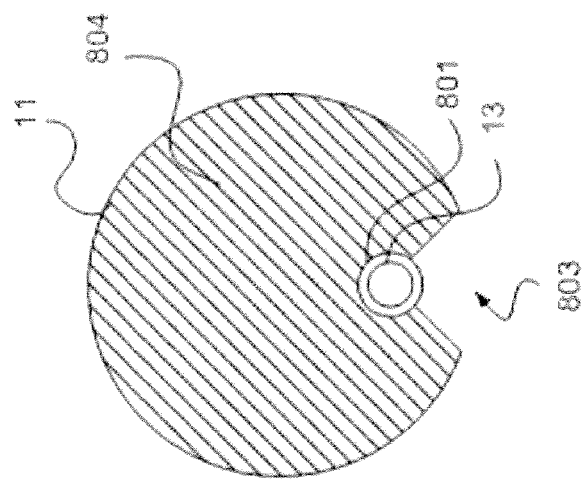
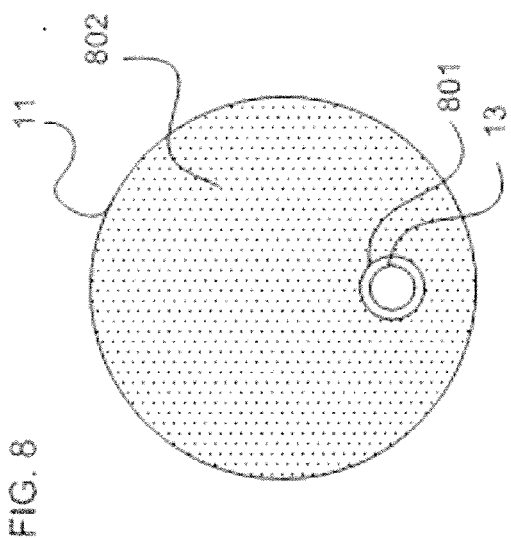

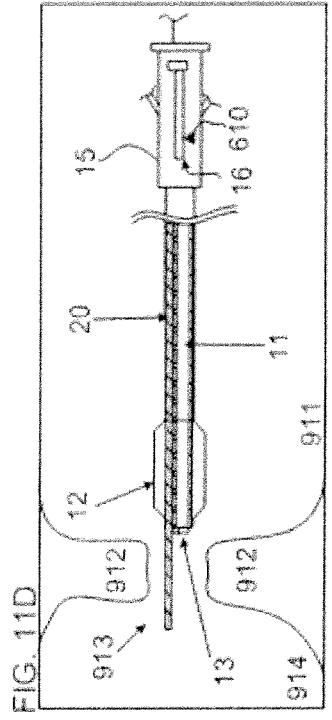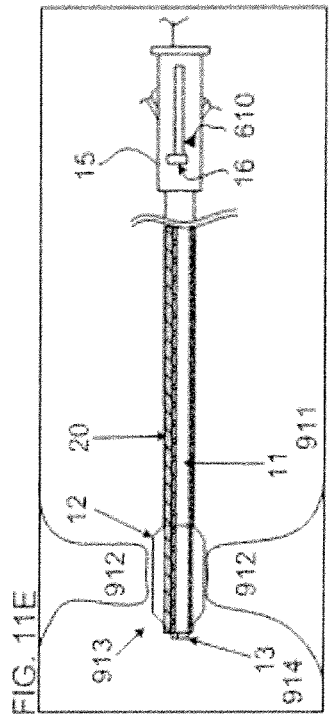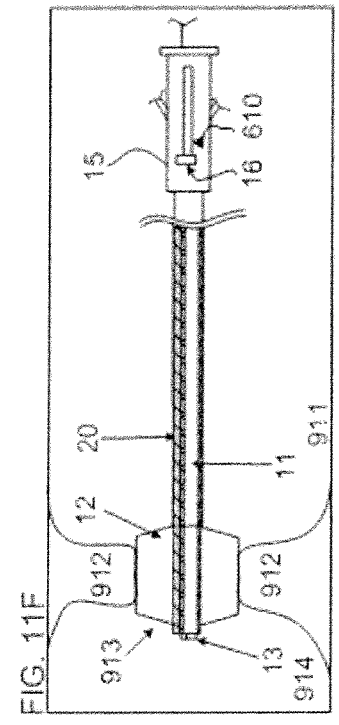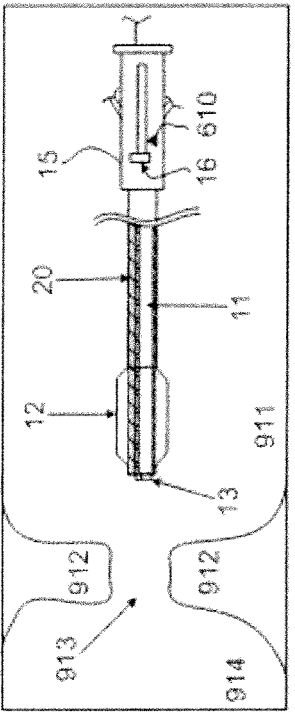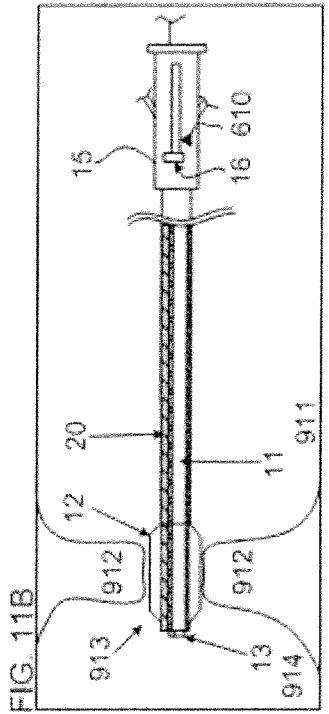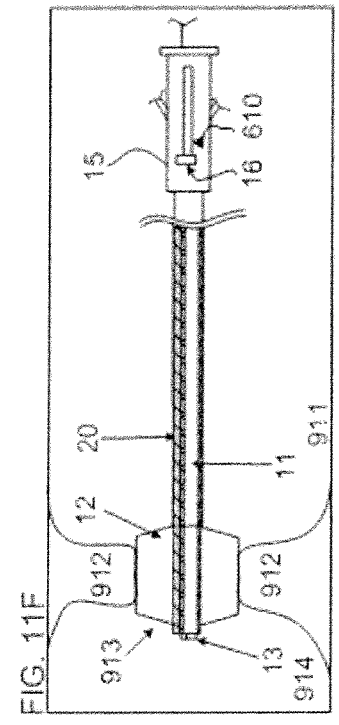

METHODS FOR TREATING SINUS OSTIA USING BALLOON CATHETER DEVICES HAVING A SLIDABLE BALLOON PORTION

BACKGROUND

1. Technical Field

The present disclosure relates to an otorhinolaryngological treatment method to be used for treatment of sinusitis and the like.

2. Description of Related Art

A paranasal sinus is an intraosseous cavity adjacent to a nasal cavity, and communicates with the nasal cavity through a small hole called the natural ostium. Secretions, bacteria, and the like in the paranasal sinus are excreted into the nasal cavity through the natural ostium. When the mucous membrane in the nasal cavity or paranasal sinus is swollen due to common cold-induced rhinitis or allergic rhinitis or the like, or the inside of the nasal cavity is narrowed due to deflected nasal septum or hypertrophic rhinitis or the like, the natural ostium may become stenosed and chronic inflammation may be generated in the paranasal sinus. Such a disease is called sinusitis. Conventionally, the method for treatment of sinusitis has generally been a surgical operation in which the lesion causing stenosis of the natural ostium is removed by use of forceps and a drill or the like while confirming the video image of the inside of the nasal cavity through an endoscope. In recent years, however, a sinusitis treatment method based on the use of a balloon catheter and not including a surgical operation has been developed, and this method has been drawing attention from the viewpoint of minimal invasiveness to the patient.

In the treatment method developed recently, a guide wire and a balloon catheter are sequentially inserted into the nasal cavity, and, after it is confirmed that the balloon catheter has been disposed in the natural ostium (for example, using a radioscopic method), the balloon catheter is expanded to force open the stenosed part of the natural ostium. According to this treatment method, the communicating passage between the nasal cavity and the paranasal sinus can be recovered without significant bleeding in the nasal cavity or damage to the mucous membrane. In connection with this technique, International Patent Publication No. WO 2006/034008 proposes a balloon catheter in which a plurality of radiopaque markers for marking the balloon proximal end, distal end and the like are disposed on the inner surface of the balloon. On the other hand, from the viewpoint of prevention of exposure of the patient to X-rays, there is an increasing demand for a balloon catheter and method of using such which enables easy positioning of the balloon inside the nasal cavity without relying on radioscopy. Some such catheter devices and methods are generally discussed in U.S. Patent Publication Nos. 2012/0253114 and 2012/0253123.

SUMMARY

It is an object of the present invention to provide otorhinolaryngological treatment methods in which positioning of an expansion body inside a nasal cavity can be easily carried out without need for radioscopy.

In an embodiment of the present invention, a method comprising: providing a balloon catheter device that comprises a balloon portion that is slidably disposed on a guide member, wherein the balloon portion is slidable from a first position with a distal end of the balloon portion at an extreme distal end of the guide member, to a second position with the distal end of the balloon portion at a predetermined length from the extreme distal end of the guide member, and wherein a camera is disposed at a distal end of the balloon portion such that the camera slides with the balloon portion; locating the balloon portion within a paranasal sinus ostium while the balloon portion is in the first position such that the distal end of the balloon portion is at a distal end of the paranasal sinus ostium; inflating the balloon portion while the balloon portion is located in the paranasal sinus ostium such that at least a portion of the paranasal sinus ostium is dilated; sliding the balloon portion back to the second position while leaving the distal end of the guide member at the distal end of the paranasal sinus ostium; and viewing an image provided by the camera to determine whether an entirety of the paranasal sinus ostium has been dilated.

In another embodiment of the present invention, a method comprises: providing a balloon catheter device that comprises a balloon portion and a camera, wherein the camera is slidably disposed in the balloon catheter device, and wherein the camera is slidable from a first position at an extreme distal end of the balloon portion, to a second position at a predetermined length from the extreme distal end of the balloon portion; locating the balloon portion within a paranasal sinus ostium while the camera is in the first position such that the end of the balloon portion and the camera are at a distal end of the paranasal sinus ostium; inflating the balloon portion while the balloon portion is located in the paranasal sinus ostium such that at least a portion of the paranasal sinus ostium is dilated; sliding the camera back to the second position while leaving the distal end of the balloon portion at the distal end of the paranasal sinus ostium; and viewing an image provided by the camera to determine whether an entirety of the paranasal sinus ostium has been dilated.

BRIEF DESCRIPTION OF THE DRAWINGS

FIGS. 2A-B show a longitudinal sectional view of a balloon catheter device that can be used in embodiments of the present invention, FIG. 2A showing the device in a non-expanded state, and FIG. 2B showing the device in an expanded state.

FIGS. 4A-B show a longitudinal sectional view of a balloon catheter device that can be used in some embodiments of the present invention, FIG. 4A showing the device with a balloon in a first position at the extreme distal end of the catheter, and FIG. 4B showing the device with a balloon in a second position approximately one balloon length proximal of the extreme distal end of the catheter.

FIGS. 5A-B show a balloon catheter device that can be used in some embodiments of the present invention with the distal end in longitudinal sectional view and the proximal end in schematic view, FIG. 5A showing the device with the device with a balloon in a first position and a slide control in a first position, and FIG. 5B showing the device with a balloon in a second position and a slide control in a second position.

FIGS. 6A-I show balloon catheter devices that can be used in some embodiments of the present invention with the proximal end in schematic view. FIGS. 6A, 6B, and 6C show a balloon catheter device using visual markers along a slide control with the slide control in a first, second, and third position, respectively. FIGS. 6D, 6E, and 6F show a balloon catheter device using a click notch along a slide control with the slide control in a first, second, and third position, respectively. FIGS. 6G, 6H, and 6I show a balloon catheter device using a line change along a slide control with the slide control in a first, second, and third position, respectively.

FIG. 8 shows a cross sectional view of a balloon catheter device that can be used in some embodiments of the present invention, demonstrating uses of opaque materials and a slotted catheter as may be useful in some embodiments.

FIG. 9A shows the positioning of the balloon catheter with the balloon in the most distal position. FIG. 9B shows approach of the distal end of the balloon catheter to the nasal cavity. FIG. 9C shows insertion of the distal end of the balloon catheter into the nasal cavity. FIG. 9D shows approach of the distal end of the balloon catheter to an opening of a paranasal sinus ostium. FIG. 9E shows insertion of the balloon into the paranasal sinus ostium. FIG. 9F shows inflation of the balloon. FIG. 9G shows deflation of the balloon. FIG. 9H shows sliding of the balloon to a second position and viewing of the nasal cavity through the camera.

FIG. 10A shows the positioning of the balloon catheter with the balloon in the most distal position. FIG. 10B shows approach of the distal end of the balloon catheter to the nasal cavity. FIG. 10C shows insertion of the distal end of the balloon catheter into the nasal cavity. FIG. 10D shows approach of the distal end of the balloon catheter to an opening of a paranasal sinus ostium. FIG. 10E shows insertion of the balloon into the paranasal sinus ostium. FIG. 10F shows inflation of the balloon. FIG. 10G shows deflation of the balloon. FIG. 10H shows sliding of the camera to a second position and viewing of the nasal cavity through the camera.

FIGS. 11A-F show a method of treating an obstructed paranasal sinus ostium according to some embodiments of the invention. FIG. 11A shows approach of the distal end of the balloon catheter to an opening of a paranasal sinus ostium with the balloon and camera in a first position. FIG. 11B shows insertion of the balloon into the paranasal sinus ostium. FIG. 11C shows sliding of the balloon and camera to a second position. FIG. 11D shows sliding of the balloon and camera to a third position. FIG. 11E shows sliding the balloon and camera back to the first position. FIG. 11F shows inflation of the balloon.

DETAILED DESCRIPTION OF THE PREFERRED EMBODIMENTS

Figure 1:
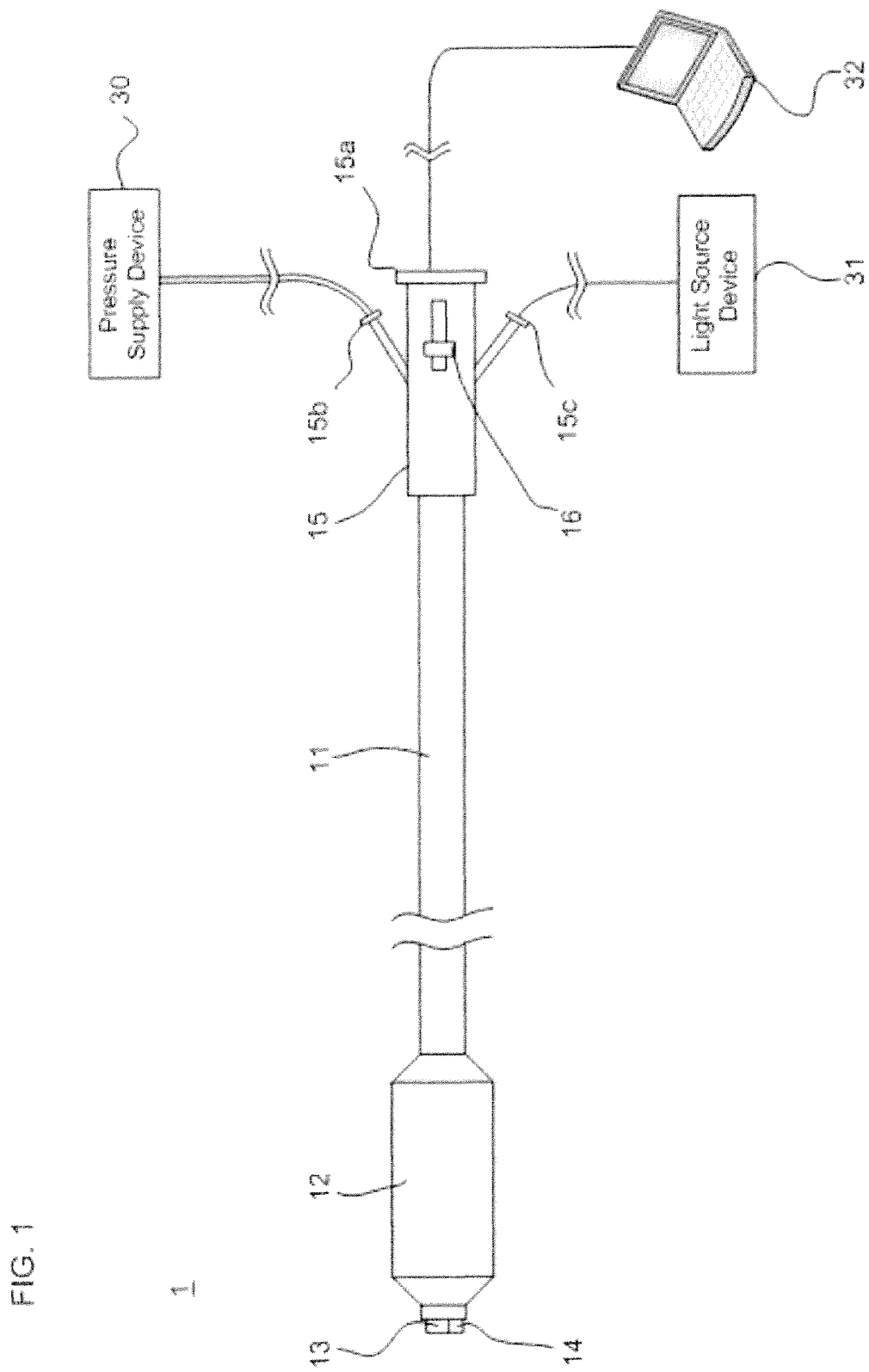
FIG. 1 is a schematic view of a treatment system as used in some embodiments of the present invention.

Embodiments of the present invention are described below referring to the drawings. For convenience of description, the dimensional ratios among components in each of the drawings as well as the dimensional ratios of the same components among the plurality of drawings are modified as required, so that they are not necessarily coincident with the actual ratios.
I. Structure of Treatment Device According to the Present Invention FIG. 1 is a schematic illustration of the general structure of a treatment system including a catheter 1 as a treatment device according to a first embodiment of the present invention. As shown in FIG. 1, the catheter 1 includes a first elongated body 11 constituting a main body thereof, a balloon 12 as an expansion body for forcing open a stenosed part of a natural ostium, a CCD camera 13 as imaging unit for obtaining an image of the inside of a nasal cavity, an LED light 14 as a lighting unit for illuminating the inside of the nasal cavity, and a hub 15 having the function of a proximal operating section to be operated by the operator as well as the function as a connection port for connection to an external apparatus. Hub 15 has a slide control 16.

Here, the term "CCD camera" means a digital video camera using a CCD image sensor as an imaging element. The hub 15 includes an image port 15a as the connection port for connection to the external apparatus, a pressure supply port 15b, and a light supply port 15c. The ports 15a-15c are described in more detail below. The catheter 1 may be inserted into the patient's nasal cavity from its end portion where the CCD camera 13 is disposed, to be used for treatment of sinusitis. In the following description, the end portion of the catheter 1 for insertion into the nasal cavity will be referred to as distal end, and the end portion on the opposite side will be referred to as proximal end.

As shown in FIG. 1, the balloon catheter 1 is connected to a display device 32 such as an LCD through the image port 15a of the hub 15, to a pressure supply device 30 such as an indeflator through the pressure supply port 15b, and to a light power source device 31 through the light supply port. Here, the display device 32 displays thereon an image obtained by the CCD camera 13. The pressure supply device 30 supplies the balloon 12 with a liquid or the like. The light power source device 31 supplies the LED light 14 with electric power.

The imaging unit in the present embodiment is not restricted to the CCD camera, but may be any of a digital video camera using other imaging element such as a CMOS image sensor, an image fiber for obtaining and transmitting images by means of optical fibers, and an imaging system for transmitting images by means of an objective lens and an optical system including a plurality of relay lenses. The "image obtaining plane" in the cases of using various cameras or optical imaging systems means a predetermined part of the imaging unit disposed so as confront an organ in a living body at the time of introduction into the inside of the living body, and the image obtaining plane may be a distal-end surface of a protective member of the image sensing element or a lens, for example.

The lighting unit in the present embodiment is not limited to the LED light, but may be other lighting units such as a halogen lamp and a high-intensity discharge lamp (HID lamp). Apart from the example shown in FIG. 1 where the LED lamp 14 is attached to the distal end of the catheter 1, the catheter 1 can also be configured such that light generated by the light power source device 31 is guided to its distal end through a light guide made by glass or plastic.

FIGS. 2A and 2B are enlarged illustrations of a longitudinal sectional view showing the vicinity of the distal end of the balloon catheter 1 of FIG. 1. Though not shown with specificity in FIGS. 2A and 2B, the first elongated body 11 may have multiple internal lumen for communication between CCD camera 13, LED lamp 14, and balloon 12 with the proximal portion of the catheter 1 including hub 15. As shown in FIGS. 2A and 2B, guide member 20 passes along the length of and interior to first elongated body 11, through balloon 12, and terminating with its distal end at the distal end of balloon catheter 1. As shown in FIG. 2A, the balloon 12 has a non-expanded state. As shown in FIG. 2B, the balloon 12 has an expanded state.

The change between the non-expanded state and expanded states for balloon 12 as shown in FIGS. 2A and 2B respectively may be effectuated through use of pressure supply device 30 and a lumen of first elongated body 11 in communication with balloon 12 and pressure supply device 30. FIG. 2B shows an effective length of balloon dilation 21 and a balloon length 22.

Figure 3A:
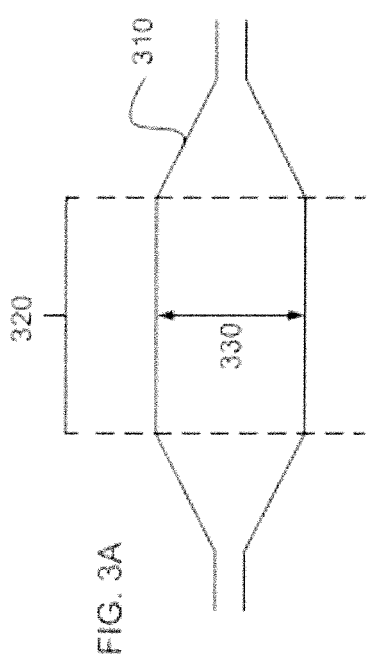
FIGS. 3A-C show a longitudinal sectional view of three balloons and an effective length of balloon dilation for each balloon.
Figure 3B:
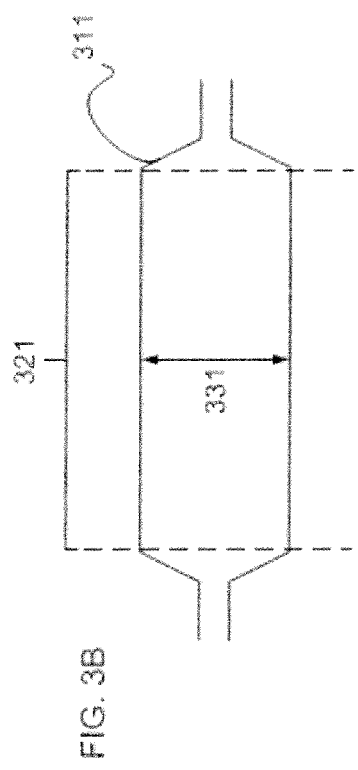
Figure 3C:
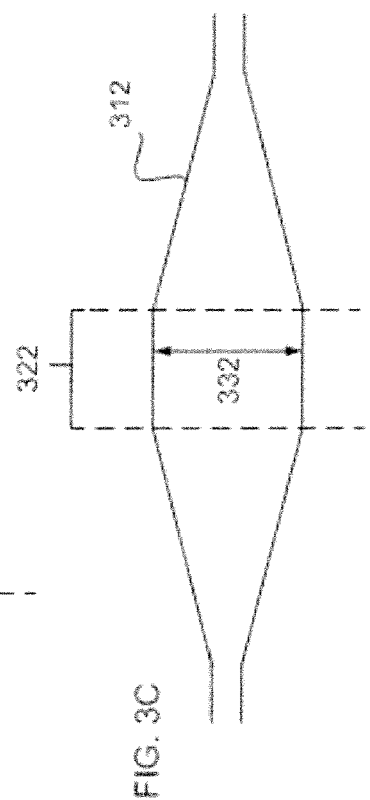

FIGS. 3A-C show a longitudinal sectional view of three balloons and an effective length of balloon dilation for each balloon. FIG. 3A shows a balloon 310 with a maximum outside diameter 330 and an effective length of balloon dilation 320. FIG. 3B shows a balloon 311 with a maximum outside diameter and an effective length of balloon dilation 321. FIG. 3C shows a balloon 312 with a maximum outside diameter 332 and an effective length of balloon dilation 322. In these embodiments, the effective length of balloon dilation is approximately the length of the balloon portion that has the maximum outside diameter of the balloon. The portion of the balloon along the effective length of balloon dilation may be referred herein as the effective portion of balloon dilation.

FIGS. 4A-B show a longitudinal sectional view of catheter 1 as shown in FIG. 1. As shown in FIG. 4A, balloon 12, CCD camera 13, and LED lamp 14 have a first position where the CCD camera 13 and LED lamp 14 are at the extreme distal end of catheter 1 and at the extreme distal end of guide member 20. In this first position as shown in FIG. 4A, the distal end of balloon 12 is also at the extreme distal end of catheter 1 and guide member 20.

As shown in FIG. 4B, balloon 12, CCD camera 13, and LED lamp 14 have a second position where the CCD camera 13 and LED lamp 14 are approximately one balloon length proximal of the extreme distal end of catheter 1 and the extreme distal end of guide member 20. In this second position as shown in FIG. 4B, the distal end of balloon 12 is a predetermined distance that is approximately one balloon length proximal of the extreme distal end of catheter 1 and guide member 20. In other embodiments, the predetermined length from the distal end of catheter 1 is an effective length of balloon dilation.

FIGS. 5A-B show catheter 1 from FIG. 1 with the distal end in longitudinal sectional view and the proximal end in schematic view. FIGS. 5A and 5B demonstrate the control of the movement of balloon 12 between the two positions shown in FIGS. 4A-B based on the manipulation of slide control 16.

As shown in FIG. 5A, balloon 12 is in a first position at the extreme distal end of catheter 1 and guide member 20. At the same time, slide control 16 is in a first position. In the example embodiment of FIG. 5A, the first position of slide control 16 has a subpart knob that is in a position at the most distal end of the slide control 16. As shown in FIG. 5B, balloon 12 is in a second position a predetermined length from the extreme distal end of catheter 1 and guide member 20. In some embodiments, the predetermined length from the extreme distal end of catheter 1 and guide member 20 where balloon 12 is in a second position may be approximately the effective length of balloon dilation 21 or the balloon length 22. At the same time, slide control 16 is in a second position. In the example embodiment of FIG. 5B, the second position of slide control 16 has a subpart knob that is in a position at the most proximal end of the slide control 16.

In other embodiments, the subpart knob of slide control 16 may move between its first and second position in the contrary direction of the movement of the balloon, i.e., the balloon is in its most distal position when the subpart knob of slide control 16 is in its most proximal position. Slide control 16 may be disposed on catheter 1 other than as shown in FIGS. 5A-B. Slide control 16 may be disposed in a non-longitudinal manner on hub 15, such as having movement along the circumference of hub 15 perpendicular to the previously shown longitudinal direction. While two distinct positions are demonstrated in FIGS. 4A-B and FIGS. 5A-B, balloon 12 and slide control 16 may be capable of holding intermediate positions between the two positions previously discussed.

In some embodiments, slide control 16 may move substantially continuously (not in discrete positions) between the most distal position and most proximal position. In these embodiments, balloon 12 may move substantially continuously in like fashion between the most distal position and most proximal position. In other embodiments, slide control 16 may move through discrete positions between the most distal position and most proximal position. In these embodiments, balloon 12 may move through discrete positions in like fashion between the most distal position and most proximal position.

As noted above, the slide control 16 may have intermediate positions between the most distal position and most proximal position. FIGS. 6A-I show balloon catheter devices that can be used in some embodiments of the present invention with the proximal end in schematic view, where there is at least one intermediate position for the slide control 16 between the most distal position and most proximal position.

FIGS. 6A, 6B, and 6C show a balloon catheter device using visual markers along a slide control with the slide control in a first, second, and third position, respectively. As shown in FIG. 6A, the slide control 16 subpart knob is in the most distal position. A visual marker 610 disposed along the slide control 16 is shown in exemplary form as a solid triangle. As shown, visual marker 610 indicates a predefined position of the slide control 16 subpart knob and the balloon 12 (not shown). FIG. 6B shows the slide control 16 subpart knob in the predefined intermediate position indicated by the visual marker 610. FIG. 6C shows the slide control 16 subpart knob in the most proximal position. The movement of slide control 16 subpart knob from the most distal to intermediate and then to most proximal positions is understood to move the balloon 12 (not shown) through most distal, intermediate, and most proximal positions, though not shown, in a manner similar to that described with reference to FIGS. 5A-B. In alternative embodiments, more than one visual marker may be disposed along the slide control 16 in order to define further intermediate positions.

FIGS. 6D, 6E, and 6F show a balloon catheter device using a click notch along a slide control with the slide control in a first, second, and third position, respectively. As shown in FIG. 6D, the slide control 16 subpart knob is in the most distal position. A click notch 611 disposed along the inner channel of slide control 16 is shown. As shown, click notch 611 indicates a predefined position of the slide control 16 subpart knob and the balloon 12 (not shown). FIG. 6E shows the slide control 16 subpart knob in the predefined intermediate position indicated by the click notch 611. In FIG. 6E, click notch 611 is not visible because it is obscured by the slide control 16 subpart knob. Click notch 611 can take any of the forms well known in the art wherein passage of a member of the slide control 16 subpart knob into the click notch 611 provides resistance to the continued movement of slide control 16 subpart knob in either the proximal or distal direction. This resistance is such to impede movement of the slide control 16 subpart knob as just noted when light force is applied by the user, but the resistance is not effective to prevent movement of the slide control 16 subpart knob when a greater amount of force is applied. FIG. 6F shows the slide control 16 subpart knob in the most proximal position. The movement of slide control 16 subpart knob from the most distal to intermediate and then to most proximal positions is understood to move the balloon 12 (not shown) through most distal, intermediate, and most proximal positions, though not shown, in a manner similar to that described with reference to FIGS. 5A-B. In alternative embodiments, more than one click notch may be disposed along the slide control 16 in order to define further intermediate positions.

FIGS. 6G, 6H, and 6I show a balloon catheter device using a line change along a slide control with the slide control in a first, second, and third position, respectively. As shown in FIG. 6G, the slide control 16 subpart knob is in the most distal position. A line change 612 disposed along the channel of slide control 16 is shown. As shown, line change 612 indicates a predefined position of the slide control 16 subpart knob and the balloon 12 (not shown). FIG. 6H shows the slide control 16 subpart knob in the predefined intermediate position indicated by the line change 612. Line change 612 as shown in the present embodiment is formed so that further advancement of the slide control 16 subpart knob in the proximal direction first requires movement of the slide control 16 subpart knob in a direction approximately perpendicular to its otherwise distal-proximal movement. FIG. 6I shows the slide control 16 subpart knob in the most proximal position. The movement of slide control 16 subpart knob from the most distal to intermediate and then to most proximal positions is understood to move the balloon 12 (not shown) through most distal, intermediate, and most proximal positions, though not shown, in a manner similar to that described with reference to FIGS. 5A-B. In alternative embodiments, more than one line change may be disposed along the slide control 16 in order to define further intermediate positions.

Figure 7A:
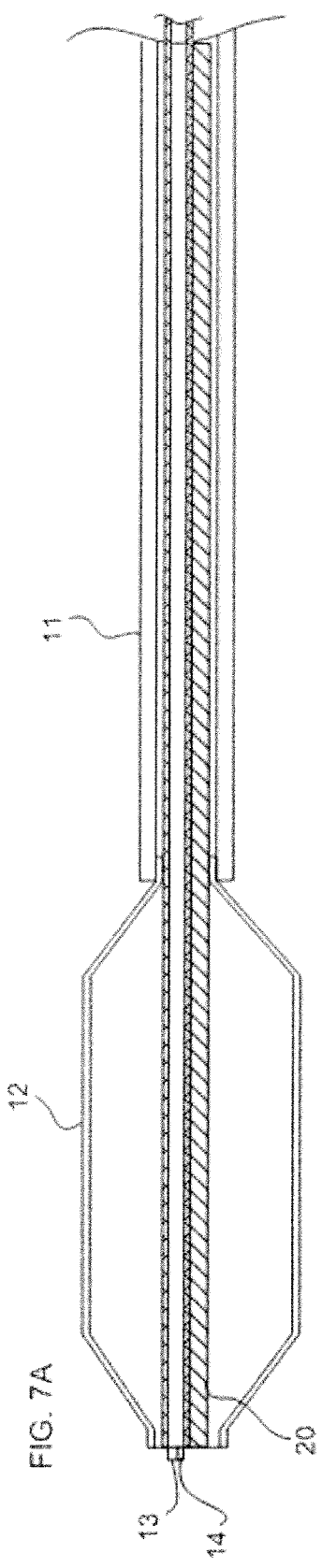
FIGS. 7A-B show a longitudinal sectional view of a balloon catheter device that can be used in some embodiments of the present invention, FIG. 7A showing the device with a camera and light source in a first position at the extreme distal end of the catheter, and FIG. 7B showing the device with a camera and light source in a second position a predetermined length proximal of the extreme distal end of the catheter.
Figure 7B:
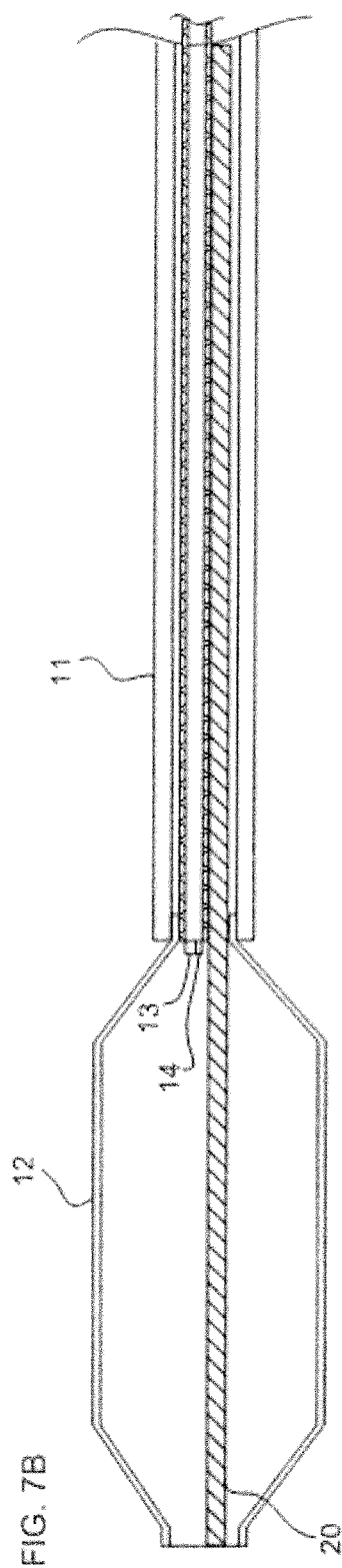

FIGS. 7A-B show a longitudinal sectional view of an alternative embodiment of catheter 1 from FIG. 1. As shown in FIG. 7A, CCD camera 13 and LED lamp 14 have a first position where the CCD camera 13 and LED lamp 14 are at the extreme distal end of catheter 1 and at the extreme distal end of guide member 20. As shown in FIG. 7B, CCD camera 13 and LED lamp 14 have a second position where the CCD camera 13 and LED lamp 14 are a predetermined length proximal of the extreme distal end of catheter 1 and the extreme distal end of guide member 20. In some embodiments, the predetermined length from the extreme distal end of catheter 1 and guide member 20 where CCD camera 13 is in a second position may be approximately the effective length of balloon dilation 21 or the balloon length 22. In this embodiment, the CCD camera 13 and LED lamp 14 may be moved between a first position and a second position independent of balloon 12. In such embodiments, balloon 12 may be substantially fixed in position relative to guide member 20.

Alternatively, in such embodiments as shown in FIGS. 7A-B balloon 12 may move between different positions as previously discussed in reference to FIGS. 4A-B and FIGS. 5A-B, while still allowing CCD camera 13 and LED lamp 14 to move between positions without moving balloon 12. In such embodiments, a second slide control 16 may be used or slide control 16 may be adapted to allow independent control of the movement of CCD camera 13 and LED lamp 14 from balloon 12.

In those embodiments such as those shown in FIGS. 7A-B where CCD camera 13 and LED lamp 14 can move to a second position without movement of balloon 12 to a similar second position, special construction of catheter 1, balloon 12, and guide member 20 may be used to allow effective use of such devices in the methods described later. Some examples of such construction are shown in FIG. 8. As shown in FIG. 8, elements such as first elongated member 11 may be made of substantially translucent material 802 so that CCD camera 13 inside an internal lumen 801 of elongated member 11 may view the area external to catheter 1 without obstruction of view from the other materials of the catheter. In other embodiments, non-translucent material 804 may be used in combination with longitudinal slot 803 passing along at least the distal end of first elongated body 11 where CCD camera 13 is able to directly view the area external to catheter 1 through the longitudinal slot 803 when CCD camera 13 is in a second position approximately one balloon length proximal of the distal end of catheter 1. Substantially translucent material 802 and longitudinal slot 803 may be used in combination as shown in FIG. 8. While FIG. 8 shows only a single lumen 801 of first elongated member 11, other lumen may exist therein especially for LED lamp 14 and fluid communication between balloon 12 and hub 15.

II. A First Method for Treatment of an Obstructed Paranasal Sinus Ostium

FIGS. 9A-H show a method of treating an obstructed paranasal sinus ostium according to some embodiments of the invention.

Figure 9A:
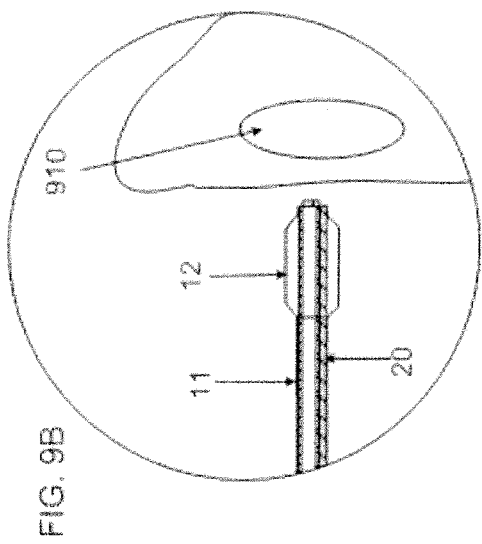
FIGS. 9A-H show a method of treating an obstructed paranasal sinus ostium according to some embodiments of the invention.
Figure 9B:
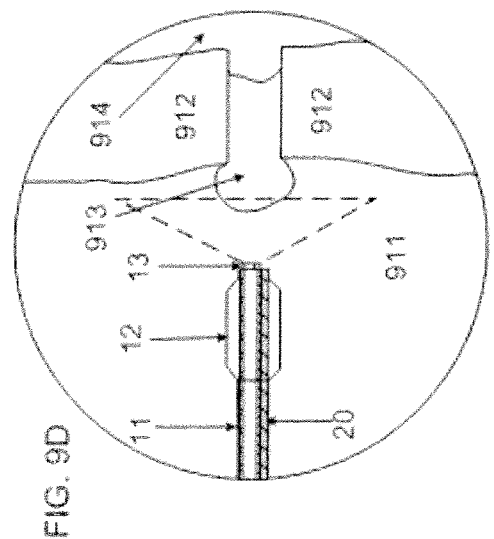
Figure 9C:
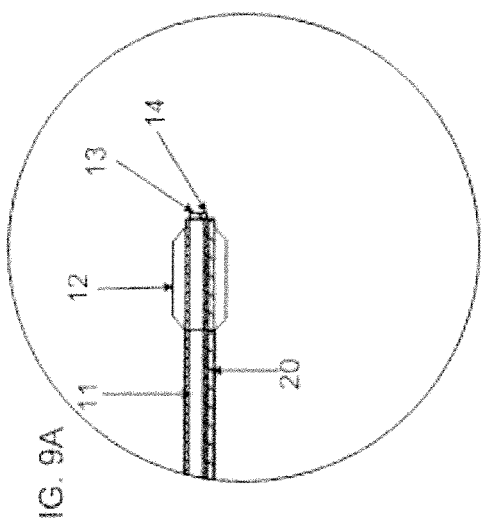

FIG. 9A shows the positioning of the balloon catheter 1 with the balloon 12 in a first position where the distal end of the balloon 12 is at the extreme distal end of catheter 1 and guide member 20. The catheter distal end is positioned to enter the nasal cavity through nasal vestibule 910 as shown in FIG. 9B. As shown in FIG. 9C, the catheter 1 is advanced into the nasal cavity through nasal vestibule 910 so that balloon 12, CCD camera 13, and LED light 14 fully enter the nasal cavity.

Figure 9D:
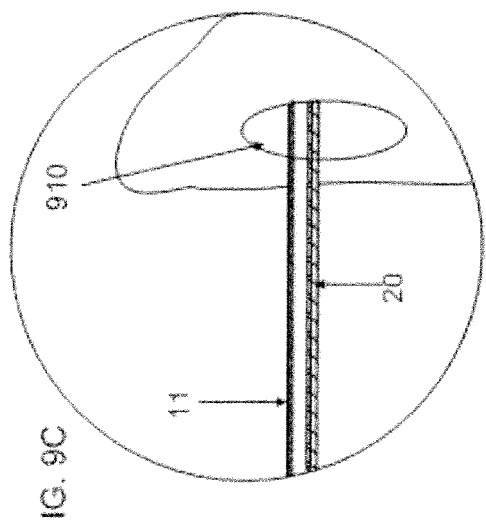

FIG. 9D shows approach of the distal end of the balloon catheter 1 to an opening of a paranasal sinus ostium 913. As shown, the distal end of the balloon catheter 1 is located in a nasal cavity 911. Using CCD camera 13, the operator views the opening of a paranasal sinus ostium 913 that connects nasal cavity 911 to paranasal sinus 914. As depicted in FIG. 9D, paranasal sinus ostium 913 passes through tissue 912. The tissue 912 in FIG. 9D is shown cut away to allow viewing of the inside of paranasal sinus ostium 913.

Figure 9F:
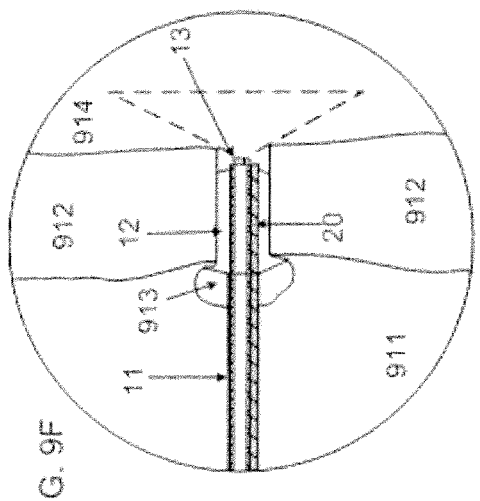
Figure 9H:
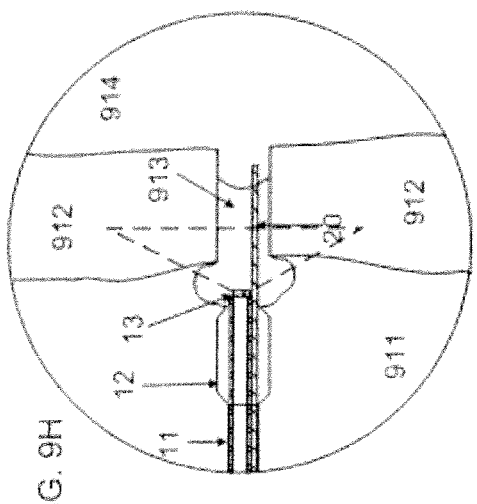
Figure 9E:
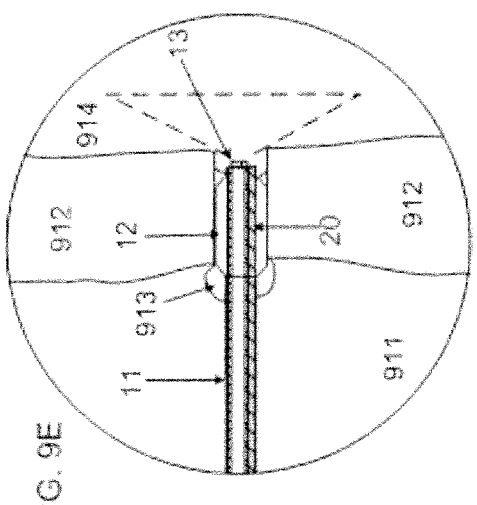

FIG. 9E shows insertion of the balloon 12 into the paranasal sinus ostium 913. As shown, the operator inserts the distal end of the balloon catheter 1 including balloon 12, CCD camera 13, LED light 14, and the distal end of guide member 20 into the paranasal sinus ostium 913. As the operator is advancing the distal end of the balloon catheter 1 through the paranasal sinus ostium 913, the tissue making up the internal walls of the paranasal sinus ostium 913 is visible using CCD camera 13. For viewing the internal walls of the paranasal sinus ostium 913, it can be advantageous for CCD camera 13 to be a wide-angle viewing camera or an oblique viewing camera. Such types of cameras make positioning of the distal end of the balloon catheter 1 easier and more effective as it is easier to see parts of the internal walls of the paranasal sinus ostium 913 that are near the extreme distal end of the balloon catheter 1. The operator may decide to stop advancing the distal end of balloon catheter 1 through paranasal sinus ostium 913 when the tissue making up the internal walls of the paranasal sinus ostium 913 is no longer visible, indicating that the CCD camera 13 and thus the extreme distal end of balloon catheter 1 have reached the other opening, the opening into the paranasal sinus 914, of paranasal sinus ostium 913.

Figure 9G:
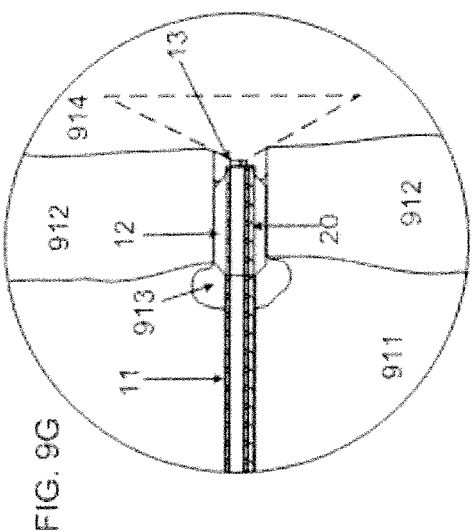

FIG. 9F shows inflation of the balloon 12. Once balloon 12 is positioned in the paranasal sinus ostium 913, the operator changes balloon 12 to its expanded state as shown in FIG. 9F. This expansion is effective to correct the stenosis of the ostium, as shown by the larger size of the paranasal sinus ostium in FIG. 9F as opposed to FIG. 9E. Once treatment by means of expansion is complete, the operator returns balloon 12 to its non-expanded state as shown in FIG. 9G.

FIG. 9H shows sliding of the balloon 12 to a second position and viewing of the nasal cavity 911 through the CCD camera 13. As shown, the operator slides balloon 12, CCD camera 13, and LED lamp 14 to a second position that is approximately one balloon length proximal of the extreme distal end of guide member 20. As depicted in FIG. 9H, guide member 20 remains in substantially the same position despite the movement of the other elements to their second position.

Once the balloon 12, CCD camera 13, and LED lamp 14 are in the second position, the operator view the area immediately in front of the CCD camera 13. As mentioned previously, having CCD camera 13 configured as a wide-angle viewing camera or an oblique viewing camera can be advantageous in this situation. If the operator is able to view the tissue making up the inside wall of nasal cavity 911, then the operator is able to determine that the balloon 12 was of sufficient length to treat the entire length of the paranasal sinus ostium 913 given that it was previously positioned at the far end of the paranasal sinus ostium 913 and now is one balloon length away from that position. In a slight variation of the step just described, the operator may determine that the entire length of the paranasal sinus ostium 913 was treated if the operator is able to view the opening to nasal cavity 911, of paranasal sinus ostium 913.

In some embodiments, if the operator determines that the previous expansion was not effective to treat the entire length of the paranasal sinus ostium 913, the operator may take further steps to treat the rest of the paranasal sinus ostium 913. In one embodiment, after determining that the entire length of the paranasal sinus ostium 913 was not treated due to the inability to see the tissue of sinus cavity 911, the operator changes the balloon 12 to its expanded state while the balloon 12, CCD camera 13, and LED lamp 14 are still in their second position one balloon length proximal of the extreme distal end of guide member 20. In other embodiments, the operator may perform the steps described with respect to FIG. 9H before expanding the balloon 12 as described with respect to FIG. 9F. By performing the steps in this order, the operator can determine in advance of treatment whether the expansion of balloon 12 will be effective to treat the entire paranasal sinus ostium 913.

After treatment of the paranasal sinus ostium 913 is complete, the operator may remove the balloon catheter 1 from the nasal cavity, changing it to its non-expanded state first if necessary.

III. A Second Method for Treatment of an Obstructed Paranasal Sinus Ostium

FIGS. 10A-H show a method of treating an obstructed paranasal sinus ostium according to some embodiments of the invention.

Figure 10A:
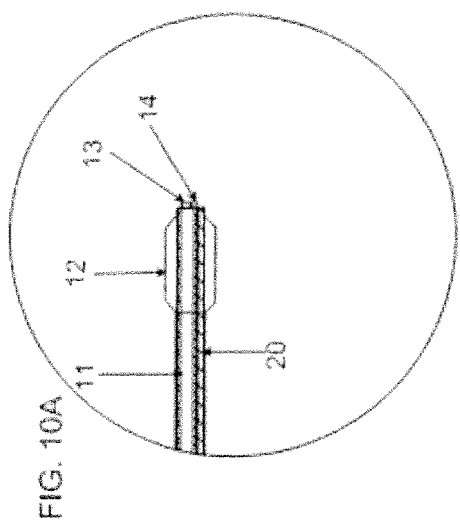
FIGS. 10A-H show a method of treating an obstructed paranasal sinus ostium according to some embodiments of the invention.
Figure 10B:
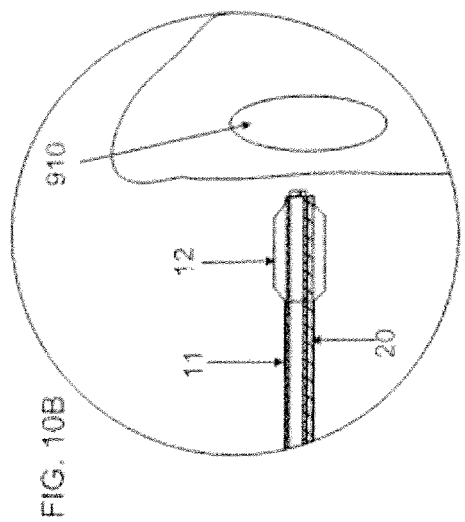
Figure 10C:
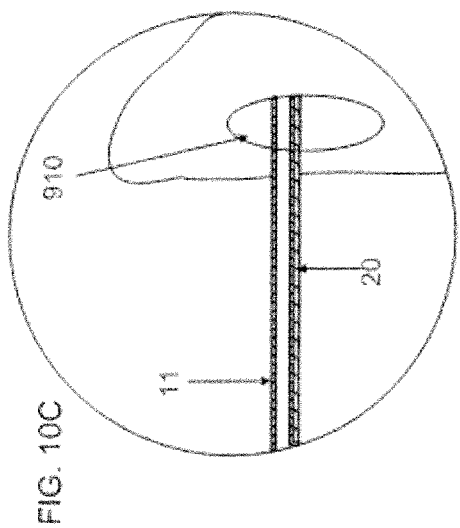

FIG. 10A shows the positioning of the balloon catheter 1 with the balloon 12 in a first position where the distal end of the balloon 12 is at the extreme distal end of catheter 1 and guide member 20. The catheter distal end is positioned to enter the nasal cavity through nasal vestibule 910 as shown in FIG. 10B. As shown in FIG. 10C, the catheter 1 is advanced into the nasal cavity through nasal vestibule 910 so that balloon 12, CCD camera 13, and LED light 14 fully enter the nasal cavity.

Figure 10D:
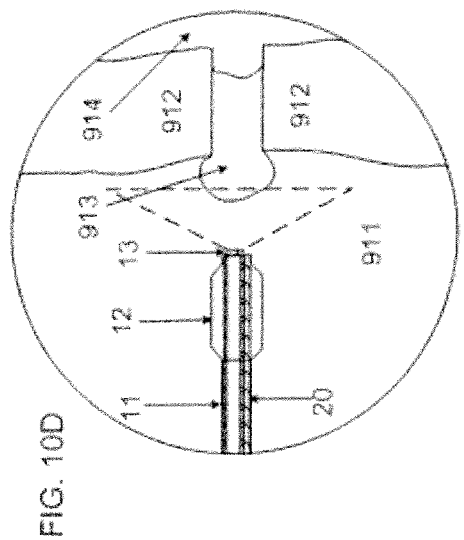

FIG. 10D shows approach of the distal end of the balloon catheter 1 to an opening of a paranasal sinus ostium 913. As shown, the distal end of the balloon catheter 1 is located in a nasal cavity 911. Using CCD camera 13, the operator views the opening of a paranasal sinus ostium 913 that connects nasal cavity 911 to paranasal sinus 914. As depicted in FIG. 10D, paranasal sinus ostium 913 passes through tissue 912. The tissue 912 in FIG. 10D is shown cut away to allow viewing of the inside of paranasal sinus ostium 913.

Figure 10F:
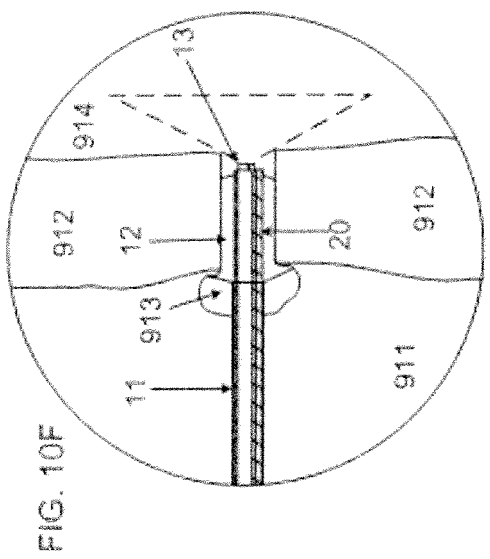
Figure 10H:
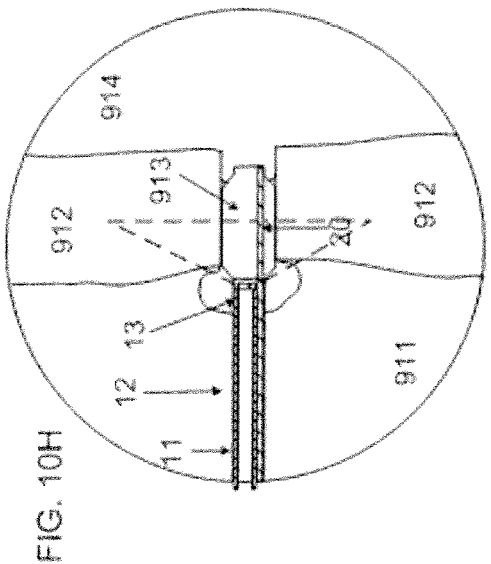
Figure 10E:
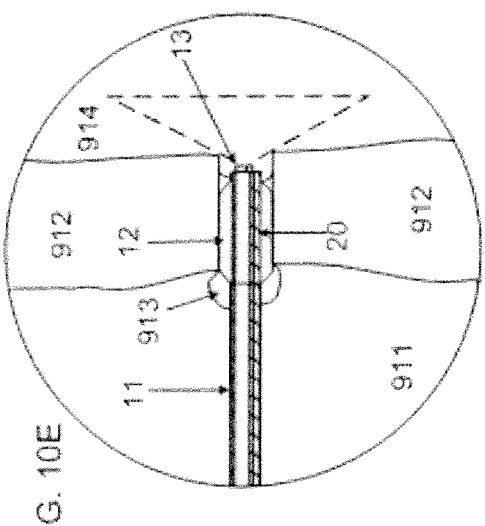

FIG. 10E shows insertion of the balloon 12 into the paranasal sinus ostium 913. As shown, the operator inserts the distal end of the balloon catheter 1 including balloon 12, CCD camera 13, LED light 14, and the distal end of guide member 20 into the paranasal sinus ostium 913. As the operator is advancing the distal end of the balloon catheter 1 through the paranasal sinus ostium 913, the tissue making up the internal walls of the paranasal sinus ostium 913 is visible using CCD camera 13. The operator may decide to stop advancing the distal end of balloon catheter 1 through paranasal sinus ostium 913 when the tissue making up the internal walls of the paranasal sinus ostium 913 is no longer visible, indicating that the CCD camera 13 and thus the extreme distal end of balloon catheter 1 have reached the other opening, the opening into the paranasal sinus 914, of paranasal sinus ostium 913.

Figure 10G:
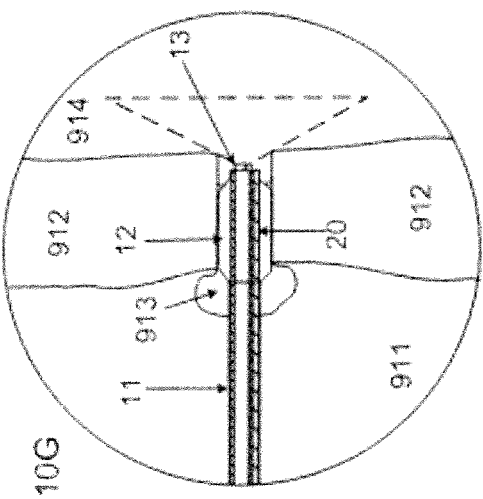

FIG. 10F shows inflation of the balloon 12. Once balloon 12 is positioned in the paranasal sinus ostium 913, the operator changes balloon 12 to its expanded state as shown in FIG. 10F. This expansion is effective to correct the stenosis of the ostium, as shown by the larger size of the paranasal sinus ostium in FIG. 10F as opposed to FIG. 10E. Once treatment by means of expansion is complete, the operator returns balloon 12 to its non-expanded state as shown in FIG. 10G.

FIG. 10H shows sliding of the CCD camera 13 to a second position and viewing of the nasal cavity 911 through the CCD camera 13. As shown, the operator slides CCD camera 13 and LED lamp 14 to a second position that is approximately one balloon length proximal of the extreme distal end of guide member 20. As depicted in FIG. 10H, guide member 20 and balloon 12 remains in substantially the same position despite the movement of the other elements to their second position.

Once the CCD camera 13 and LED lamp 14 are in the second position, the operator views the area immediately in front of and around the CCD camera 13. As mentioned previously, having CCD camera 13 configured as a wide-angle viewing camera or an oblique viewing camera can be advantageous in this situation. If the operator is able to view the tissue making up the inside wall of nasal cavity 911, then the operator is able to determine that the balloon 12 was of sufficient length to treat the entire length of the paranasal sinus ostium 913 given that the CCD camera was previously positioned at the far end of the paranasal sinus ostium 913 and now is one balloon length away from that position. In a slight variation of the step just described, the operator may determine that the entire length of the paranasal sinus ostium 913 was treated if the operator is able to view the entire opening, the opening to nasal cavity 911, of paranasal sinus ostium 913.

In some embodiments, if the operator determines that the previous expansion was not effective to treat the entire length of the paranasal sinus ostium 913, the operator may take further steps to treat the rest of the paranasal sinus ostium 913. In one embodiment, after determining that the entire length of the paranasal sinus ostium 913 was not treated due to the inability to see the tissue of sinus cavity 911, the operator moves the balloon 12 to a second position approximately one balloon length proximal of the extreme distal end of guide member 20 and changes the balloon 12 to its expanded state.

In some embodiments of the method just described, the operator may skip the step shown in FIG. 10G, i.e., the operator may decide not to change the balloon to its non-expanded state before sliding the CCD camera 13 to a second position. In other embodiments, the operator may perform the steps described with respect to FIG. 10H before expanding the balloon 12 as described with respect to FIG. 10F. By performing the steps in this order, the operator can determine in advance of treatment whether the expansion of balloon 12 will be effective to treat the entire paranasal sinus ostium 913.

After treatment of the paranasal sinus ostium 913 is complete, the operator may remove the balloon catheter 1 from the nasal cavity, changing it to its non-expanded state first if necessary.

IV. A Third Method for Treatment of an Obstructed Paranasal Sinus Ostium

FIGS. 11A-F show a method of treating an obstructed paranasal sinus ostium according to some embodiments of the invention.

FIG. 11A shows approach of the distal end of the balloon catheter 1 to an opening of a paranasal sinus ostium 913. As shown, this approach is performed with the balloon 12 and CCD camera 13 in a first position that has the distal end of the balloon 12 and the CCD camera 13 at the most distal end of the guide member 20. Accordingly, the slide control 16 subpart knob is in a first position at the most distal end of the channel of slide control 16. The embodiment shown in FIGS. 11A-F contain a visual marker 610 along the slide control 16 indicating an intermediate position as was described with reference to FIGS. 6A-C. Using CCD camera 13, the operator views the opening of a paranasal sinus ostium 913 that connects nasal cavity 911 to paranasal sinus 914. As depicted in FIG. 11A, paranasal sinus ostium 913 passes through tissue 912. The tissue 912 in FIG. 11A is shown cut away to allow viewing of the inside of paranasal sinus ostium 913.

FIG. 11B shows insertion of the balloon 12 into the paranasal sinus ostium 913. As shown, the operator inserts the distal end of the balloon catheter 1 including balloon 12, CCD camera 13, LED light 14, and the distal end of guide member 20 into the paranasal sinus ostium 913. As the operator is advancing the distal end of the balloon catheter 1 through the paranasal sinus ostium 913, the tissue making up the internal walls of the paranasal sinus ostium 913 is visible using CCD camera 13. The operator may decide to stop advancing the distal end of balloon catheter 1 through paranasal sinus ostium 913 when the tissue making up the internal walls of the paranasal sinus ostium 913 is no longer visible, indicating that the CCD camera 13 and thus the extreme distal end of balloon catheter 1 have reached the other opening, the opening into the paranasal sinus 914, of paranasal sinus ostium 913.

Once the balloon 12 and guide member 20 are placed in the paranasal sinus ostium 913, the operator can then slide the balloon 12 and CCD camera 13 to a second position as shown in FIG. 11C. As shown in FIG. 11C, the guide member 20 remains in its original place as described with reference to FIG. 11B. However, the operator slides the balloon 12 and CCD camera 13 to a second position such that the distal end of the balloon 12 and the CCD camera 13 are now at a position where the distal end of the effective portion of balloon dilation was located in FIG. 11B. The operator is able to place the balloon 12 and CCD camera 13 with ease into the second position just described because the distance of sliding necessary to reach the second position is marked by the visual indicator 610 along the slide control 16. Therefore, the operator simply slides the slide control 16 subpart knob to the position indicated by the visual indicator 610 and the balloon 12 and CCD camera 13 will reach the second position described above.

Expanding on the placement of balloon 12 and CCD camera 13 shown in FIG. 11C, it is advantageous to the operator to achieve this particular placement. The location of CCD camera 13 in FIG. 11C, as noted above, is the same position where the distal-most end of the effective portion of balloon dilation was located when the balloon 12 was in its first (i.e., distal-most) position. With CCD camera 13 in this second position, the operator is able to view using CCD camera 13, whether the entire paranasal sinus ostium 913 will be treated by the balloon 12 once inflated. This determination is possible because, with the CCD camera 13 in its second position, if the operator is able to see the tissue making up the internal walls of the paranasal sinus ostium 913, then the operator knows that the effective portion of balloon dilation portion of balloon 12, when balloon 12 is in its first position, does not extend distally of the distal-most portion of paranasal sinus ostium 913. In such a case, the entire paransal sinus ostium 913 will not be treated when the balloon 12 is dilated while in its first position. On the other hand, if when the CCD camera 13 is in its second position the operator does not see any of the tissue making up the internal walls of the paranasal sinus ostium 913, then the operator knows that the effective portion of balloon dilation of the balloon 12 extended fully distal of the paranasal sinus ostium 913, so at least the entire distal portion of the paransal sinus ostium 913 will be treated.

The operator can then slide the balloon 12 and CCD camera 13 to a third position as shown in FIG. 11D. As shown in FIG. 11D, the guide member 20 remains in its original place as described with reference to FIG. 11B. However, the operator slides the balloon 12 and CCD camera 13 to a third position such that the distal end of the balloon 12 and the CCD camera 13 are now at a position where the proximal end of the effective portion of balloon dilation for balloon 12 was located in FIG. 11B. The operator is able to place the balloon 12 and CCD camera 13 with ease into the third position just described because that position is the proximal-most position reachable by the balloon 12 and CCD camera 13. Therefore, the operator simply slides the slide control 16 subpart knob to proximal-most position along slide control 16 and the balloon 12 and CCD camera 13 will reach the third position described above.

Expanding on the placement of balloon 12 and CCD camera 13 shown in FIG. 11D, it is advantageous to the operator to achieve this particular placement. Whereas the second position was advantageous as described with reference to FIG. 11C because it allowed the operator to determine if the entire distal end of paranasal sinus ostium 913 would be treated, the third position allows a similar determination for the proximal end of paranasal sinus ostium 913. The location of CCD camera 13 in FIG. 11D, as noted above, is the same position where the proximal-most end of the effective portion of balloon dilation was located when the balloon 12 was in its first (i.e., distal-most) position. With CCD camera 13 in this third position, the operator is able to view using CCD camera 13, whether the entire paranasal sinus ostium 913 will be treated by the balloon 12 once inflated. This determination is possible because, with the CCD camera 13 in its third position, if the operator is not able to see the entire opening of paranasal sinus ostium 913 into nasal cavity 911, then the operator knows that the effective portion of balloon dilation portion of balloon 12, when balloon 12 is in its first position, does not extend proximally of the proximal-most portion of paranasal sinus ostium 913. In such a case, the entire paransal sinus ostium 913 will not be treated when the balloon 12 is dilated while in its first position. On the other hand, if when the CCD camera 13 is in its third position the operator does see the entire opening of paranasal sinus ostium 913 into nasal cavity 911, then the operator knows that the effective portion of balloon dilation of the balloon 12 extended fully proximal of the paranasal sinus ostium 913, so at least the entire proximal portion of the paransal sinus ostium 913 will be treated.

FIG. 11E shows sliding the balloon and camera back to the first position. As shown, the operator can easily slide the balloon 12 and CCD camera 13 back to their first (i.e., distal-most) position because the slide control 16 subpart knob need only be slid to its distal-most position.

FIG. 11F shows inflation of the balloon. If the steps described with respect to FIGS. 11C and 11D indicated that both the distal-most portion and the proximal-most portion of the paransal sinus ostium 913 would be dilated with the balloon 12 in its first position, then the operator can safely dilate balloon 12 knowing that the entire paransal sinus ostium 913 will be treated. If, however, either of the steps described with respect to FIGS. 11C and 11D indicated that one of the ends of the paranasal sinus ostium 913 would not be treated based on dilation of the balloon 12 in its first position, then the operator can adjust the entire balloon catheter 1 including guide member 20 to improve the placement of the effective part of balloon dilation for balloon 12 in paransal sinus ostium 913. Upon adjustment of the position of balloon catheter 1, the operator can repeat the steps described with reference to FIGS. 11B-11E in order to verify that the new position will result in treatment of the entire paranasal sinus ostium 913.

V. A Fourth Method for Treatment of an Obstructed Paranasal Sinus Ostium

Figure 12:
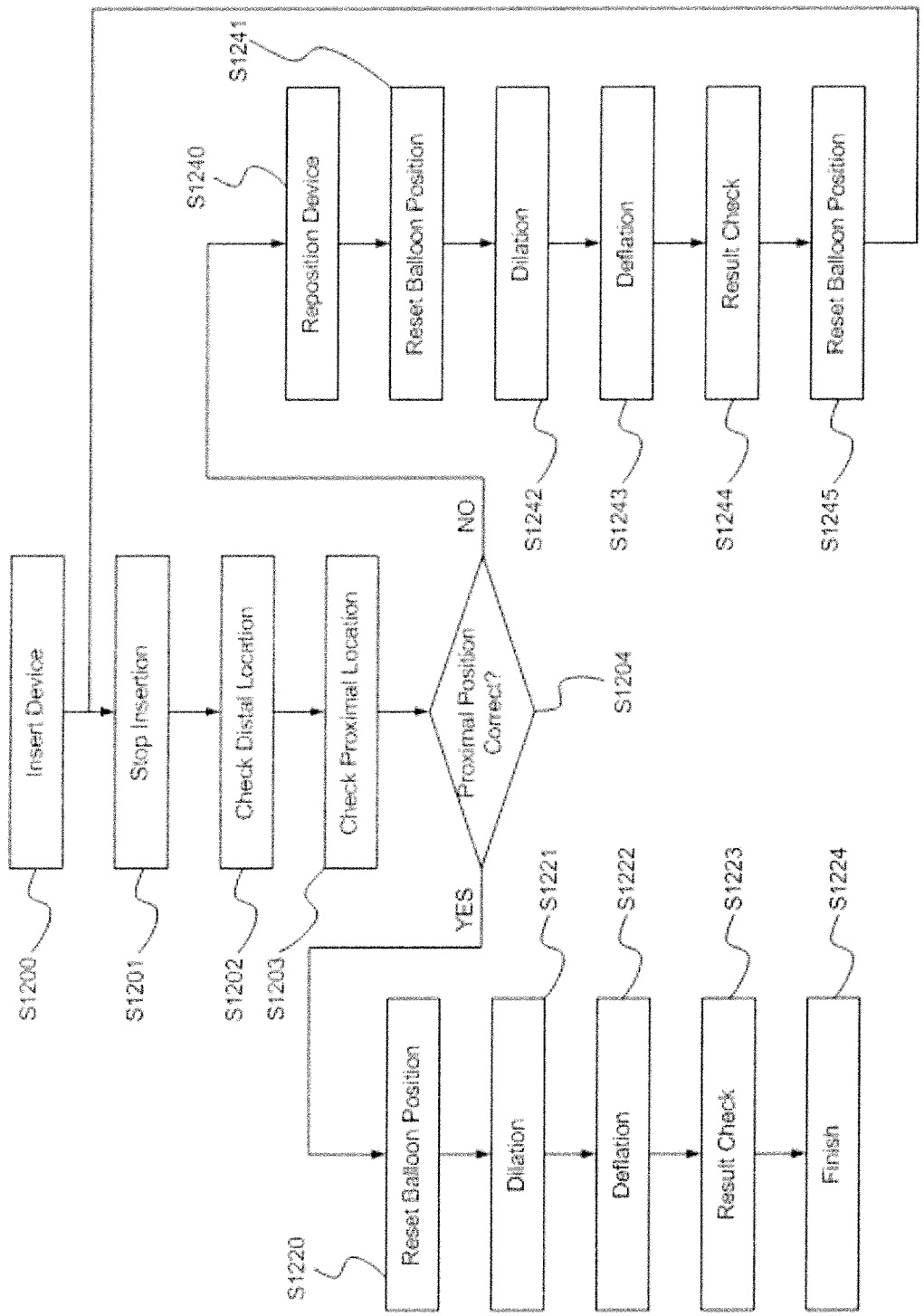
FIG. 12 shows a flowchart demonstrating a method of treating an obstructed paranasal sinus ostium according to some embodiments of the invention.

FIG. 12 shows a flowchart demonstrating a method of treating an obstructed paranasal sinus ostium according to some embodiments of the invention. This method will be described where possible with reference to the features of previous figures including FIG. 11.

As shown in FIG. 12, the method according to this embodiment begins in step S1200. In this step, the operator positions the balloon 12 and camera 13 of a balloon catheter 1 in a distal-most position. This is the "first" position as used in this method. The operator inserts the distal end of the balloon catheter 1 into the nasal cavity 911 of the patient until it is near the opening of a target paranasal sinus ostium 913. This target paranasal sinus ostium is a conduit to a target paranasal sinus 914. The opening of the target paranasal sinus ostium 913 into the nasal cavity 911 for this method is called the proximal opening of the target paranasal sinus ostium 913. The opening of the target paranasal sinus ostium into the target paranasal sinus 914 for this method is called the distal opening of the target paranasal sinus ostium 913.

In step S1201, the operator inserts the distal end of balloon catheter 1 into the target paranasal sinus ostium 913 through its proximal opening. The operator continues insertion as such until the distal portion of balloon catheter 1 enters the target paranasal sinus. The operator is able to determine that such entry has occurred either when an interior wall of the target paranasal sinus is visible or when the inside walls of the target paranasal sinus ostium 913 are no longer visible.

In step S1202, the operator checks the distal positioning of the balloon 12. When the balloon is in its first position, there is a distal-most position of its effective portion of dilation, which for this method is called the "distal-most point of treatment." When the balloon is in its first position, there is a proximal-most position of its effective portion of dilation, which for this method is called the "proximal-most point of treatment." With the balloon 12 in its first position, the operator slides the balloon 12 and camera 13 to a second position using slide control 16. When in its second position, the distal-most end of the balloon 12 and camera 13 are located approximately at the distal-most point of treatment.

With the balloon 12 and camera 13 so situated, the operator views an image from the camera 13 to determine whether the target paranasal sinus ostium 913 will be fully treated through to its distal opening. The operator makes this determination by looking for whether the distal opening of the target paranasal sinus ostium 913 is visible from the camera 13. If the distal opening of the target paranasal sinus ostium 913 is so visible, then the camera 13 must now be inside the paranasal sinus ostium 913, and as such, the effective portion of dilation for balloon 12 would not treat the distal-most portion of target paranasal sinus ostium 913 because it only extends to the distal-most point of treatment when the balloon 12 is in its first position. If, however, the operator determines that the distal opening of the target paranasal sinus ostium 913 is not visible, then the effective portion of dilation for balloon 12 extends distally out of the target paranasal sinus ostium 913 when in its first position and as such would treat the entire distal end of that ostium 913 when inflated in the first position.

In step S1203, the operator checks the proximal positioning of the balloon 12. With the balloon 12 in its second position, the operator slides the balloon 12 and camera 13 to a third position using slide control 16. When in its third position, the distal-most end of the balloon 12 and camera 13 are located approximately at the proximal-most point of treatment.

With the balloon 12 and camera 13 so situated, the operator views an image from the camera 13 to determine whether the target paranasal sinus ostium 913 will be fully treated through to its proximal opening. The operator makes this determination by looking for whether the proximal opening of the target paranasal sinus ostium 913 is visible from the camera 13. If the proximal opening of the target paranasal sinus ostium 913 is not visible, then the camera 13 must now be inside the paranasal sinus ostium 913, and as such, the effective portion of dilation for balloon 12 would not treat the proximal-most portion of target paranasal sinus ostium 913 because it only extends to the proximal-most point of treatment when the balloon 12 is in its first position. If, however, the operator determines that the proximal opening of the target paranasal sinus ostium 913 is visible, then the effective portion of dilation for balloon 12 extends proximally out of the target paranasal sinus ostium 913 when in its first position and as such would treat the entire proximal end of that ostium 913 when inflated in the first position.

In step S1204, the operator decides whether to continue to step S1220 or step S1240. In this embodiment of the method, the operator continues to step S1220 if the proximal opening of the target paranasal sinus ostium was visible in step S1203. In this embodiment of the method, the operator continues to step S1240 if the proximal opening of the target paranasal sinus ostium was not visible in step S1203.

In step S1240, the operator repositions the balloon catheter 1. With the balloon 12 and camera 13 still in the third position, the operator pulls the balloon catheter 1 in the proximal direction until the proximal opening of the target paranasal sinus ostium 913 is visible. At this position, the operator knows that the entire proximal end of the target paranasal sinus ostium will be treated when the balloon 12 is inflated in its first position, because the effective portion of dilation extends to the proximal-most point of treatment, which has moved proximally during this step and is now what the camera 13 is viewing.

In step S1241, the operator leaves balloon catheter 1 in its present position but slides the balloon 12 and camera 13 back to their first position using slide control 16.

In step S1242, the operator dilates balloon 12 using pressure supply device 30. This dilation is effective to treat at least the proximal-most portion of the target paranasal sinus ostium 913.

In step 1243, the operator deflates balloon 12 using pressure supply device 30.

In step 1244, the operator checks the results of the dilation by sliding the balloon 12 and camera 13 to their third position. In this position, the operator is able to view the proximal-most portion of the target paranasal sinus ostium that was just treated.

In step S1245, the operator leaves balloon catheter 1 in its present position but slides the balloon 12 and camera 13 back to their first position using slide control 16.

After step S1245, the operator returns to the sequence of steps beginning at step S1201. However, when performing steps S1201, S1202, S1203, and S1204, the operator will no longer be looking for the proximal opening of the target paranasal sinus ostium 913 when checking the proximal location of the balloon. This is because the proximal-most portion of target paranasal sinus ostium 913 extending from the proximal opening of that ostium inwards for approximately the effective length of balloon dilation 21 has now been treated. Therefore, in steps S1201 through S1204, the operator will be looking to position balloon 12 so that, when in its first position, the proximal-most point of treatment is just proximal of the previous distal-most point of treatment. That is, this embodiment of the method treats the proximal-most untreated length 21 of ostium 913 repeatedly until the entire ostium 913 is treated through to its distal opening.

In step S1220, the operator leaves balloon catheter 1 in its present position but slides the balloon 12 and camera 13 back to their first position using slide control 16.

In step S1221, the operator dilates balloon 12 using pressure supply device 30. This dilation is effective to treat the distal-most portion of the target paranasal sinus ostium 913. This is true because as noted above, this method treats the ostium 913 from its proximal opening to its distal opening, and the decision at S1204 will only result in this branch of the method being executed if this inflation dilation will be effective to treat the entire untreated portion of ostium 913.

In step 1222, the operator deflates balloon 12 using pressure supply device 30.

In step 1223, the operator checks the results of the dilation by sliding the balloon 12 and camera 13 to their third position. In this position, the operator is able to view the proximal-most portion of the target paranasal sinus ostium that was just treated.

In step 1224, the operator finishes the method by removing the balloon catheter 1 from the patient's body.

Other embodiments of the method do not require performance of the above described steps in the order described above. For instance, some embodiments of the method may perform dilation beginning from the distal end of the target paranasal sinus ostium 913 and continuing to the proximal end. In other embodiments some of the steps just described may be skipped, such as steps S1202 or S1244.

According to the method of the present invention as above-described, the expansion body (balloon), particularly the effective expansive section of the expansion body (balloon) can be disposed over substantially the whole length of the stenosed part, so that the whole of the stenosed part can be pushed open when the expansion body (balloon) is expanded. According to the above-mentioned method, therefore, the stenosed part of the natural ostium can be pushed open more assuredly, so that a therapeutic effect on sinusitis can be enhanced. Besides, according to the above-described method, the catheter can be effectively prevented from being advanced excessively into the paranasal sinus cavity, so that safety in treatment of sinusitis can be enhanced. Furthermore, according to the method of the present invention, the expansion body in the inside of the nasal cavity can be positioned easily and accurately, and the stenosed part of the paranasal sinus cavity can be dilated assuredly and easily, by use of a simple device such as an endoscope, without using any special apparatus such as an X-ray apparatus. In addition, the method according to the present invention is a minimally invasive method based on the use of a catheter, which promises less-invasiveness to the patient.

The present invention may be practiced or embodied in still other ways without departing from the spirit or essential character thereof. The preferred embodiments described herein are therefore illustrative and not restrictive, the scope of the invention being indicated by the appended claims and all variations which fall within the meaning of the claims are intended to be embraced therein.

What is claimed is:
1. A method comprising:
providing a balloon catheter device that comprises a balloon portion that is slidably disposed on a guide member, wherein the balloon portion is slidable from a first position with a distal end of the balloon portion at an extreme distal end of the guide member, to a second position with the distal end of the balloon portion at a predetermined length from the extreme distal end of the guide member, and wherein a camera is disposed at a distal end of the balloon portion such that the camera slides over the guide member with the balloon portion;
advancing the balloon portion to a location within a paranasal sinus ostium while the balloon portion is in the first position until the distal end of the balloon portion is at a distal end of the paranasal sinus ostium;
inflating the balloon portion while the balloon portion is located in the paranasal sinus ostium such that at least a portion of the paranasal sinus ostium is dilated;
sliding the balloon portion back to the second position while leaving the distal end of the guide member at the distal end of the paranasal sinus ostium; and
while the balloon portion is located in the second position, viewing an image provided by the camera to determine whether an entirety of the paranasal sinus ostium has been dilated.

2. The method of claim 1, further comprising, after advancing the balloon portion to the location within the paranasal sinus ostium, and before inflating the balloon portion, sliding the balloon portion back to the second position and checking whether a proximal end of the paranasal sinus ostium is visible or not.

3. The method of claim 1, wherein the predetermined length is a length of an effective part of the balloon portion.

4. The method of claim 1, wherein the predetermined length is approximately a length of the balloon portion.

5. The method of claim 1, wherein the determination of whether the entirety of the paranasal sinus ostium has been dilated is made by determining whether the viewing of the image shows that the distal end of the balloon portion has entirely exited the paranasal sinus ostium.

6. The method of claim 1, further comprising deflating the balloon portion while the balloon portion is located in the paranasal sinus ostium.

7. The method of claim 6, wherein the steps of inflating the balloon portion and deflating the balloon portion are performed after the step of locating the balloon portion within the paranasal sinus ostium and before the step of sliding the balloon portion back to the second position.

8. The method of claim 7, further comprising inflating the balloon portion a second time while the balloon portion is in the second position.

9. The method of claim 1, wherein the step of locating the balloon portion within the paranasal sinus ostium is performed by viewing an inside of the paranasal sinus ostium using the camera as the balloon portion is advanced through the paranasal sinus ostium, and stopping insertion of the balloon portion into the paranasal sinus ostium when the inside of the paranasal sinus ostium is no longer visible using the camera.

10. The method of claim 1, wherein the balloon portion is not slidable past the second position in a direction away from the distal end of the guide member.

11. The method of claim 1, wherein the paranasal sinus is a maxillary sinus.

12. The method of claim 1, wherein the paranasal sinus is a frontal sinus.

13. The method of claim 1, wherein the paranasal sinus is a sphenoid sinus.

14. A method comprising:
providing a balloon catheter device that comprises:
a balloon portion that is slidably disposed on a guide member, wherein the balloon portion is slidable between (i) a first position with a distal end of the balloon portion at an extreme distal end of the guide member, (ii) a second position with the distal end of the balloon portion at a first predetermined length from the extreme distal end of the guide member, wherein the first predetermined length is a distance between the distal end of the balloon portion and a distal end of an effective portion of dilation of the balloon portion, and (iii) a third position with the distal end of the balloon portion at a second predetermined length from the extreme distal end of the guide member, wherein the second predetermined length is a distance between the distal end of the balloon portion and a proximal end of an effective portion of dilation of the balloon portion, wherein a camera is disposed at a distal end of the balloon portion such that the camera slides with the balloon portion;

advancing the balloon portion to a location within a paranasal sinus ostium while the balloon portion is in the first position until the distal end of the balloon portion is at a distal end of the paranasal sinus ostium;

sliding the balloon portion back to the second position while leaving the distal end of the guide member at the distal end of the paranasal sinus ostium, and viewing an image provided by the camera to determine if the distal end of the paranasal sinus ostium is visible;

sliding the balloon portion back to the third position while leaving the distal end of the guide member at the distal end of the paranasal sinus ostium, and viewing an image provided the camera to determine if the proximal end of the paranasal sinus ostium is visible;

inflating the balloon portion while the balloon portion is located in the paranasal sinus ostium such that at least a portion of the paranasal sinus ostium is dilated; and viewing an image provided by the camera to determine whether an entirety of the paranasal sinus ostium has been dilated.

15. The method of claim 14, wherein the step of inflating the balloon portion is only performed when the balloon portion is in the first position.

16. The method of claim 14, wherein the step of sliding the balloon portion back to the third position is performed before the step of inflating the balloon portion.

* * * * *